United States Patent
Ostafin et al.

(10) Patent No.: US 10,751,464 B2
(45) Date of Patent: Aug. 25, 2020

(54) THERAPEUTIC RETRIEVAL OF TARGETS IN BIOLOGICAL FLUIDS

(71) Applicant: Nanoshell Company, LLC, North Salt Lake, UT (US)

(72) Inventors: Agnes Ostafin, North Salt Lake, UT (US); Hiroshi Mizukami, Pasadena, CA (US)

(73) Assignee: NANOSHELL COMPANY, LLC, North Salt Lake, UT (US)

(*) Notice: Subject to any disclaimer, the term of this patent is extended or adjusted under 35 U.S.C. 154(b) by 512 days.

(21) Appl. No.: 14/920,764

(22) Filed: Oct. 22, 2015

(65) Prior Publication Data

US 2016/0038668 A1 Feb. 11, 2016

Related U.S. Application Data

(63) Continuation-in-part of application No. 13/936,092, filed on Jul. 5, 2013, now abandoned.
(Continued)

(51) Int. Cl.
*A61M 1/36* (2006.01)
*B01F 5/06* (2006.01)
*A61M 1/32* (2006.01)

(52) U.S. Cl.
CPC ............ *A61M 1/3693* (2013.01); *A61M 1/32* (2013.01); *A61M 1/362* (2014.02);
(Continued)

(58) Field of Classification Search
CPC .............. A61M 1/3693; A61M 1/3687; A61M 2206/11; A61M 1/367; A61M 1/3615;
(Continued)

(56) References Cited

U.S. PATENT DOCUMENTS

| 4,387,848 A | 6/1983 | Kellogg et al. |
| 4,479,790 A | 10/1984 | Bocckino et al. |

(Continued)

FOREIGN PATENT DOCUMENTS

| CA | 1298822 | 4/1992 |
| CN | 101172207 | 5/2008 |

(Continued)

OTHER PUBLICATIONS

Andres, et al., "Anisotropic Calcium Phosphate Nanoparticles Coated with 2-Carboxyethylphosphonic Acid", J. Mater. Chem. vol. 16, 2006, 3964-3968.
(Continued)

*Primary Examiner* — Peter S Vasat
*Assistant Examiner* — Sara A Sass
(74) *Attorney, Agent, or Firm* — Peacock Law P.C.; Janeen Vilven

(57) ABSTRACT

Method and apparatus for removing high density particles from a biological fluid such as blood using aphaeresis. The particles are preferably sub-micron in size and denser than normally occurring components of the fluid and can be removed by a modified reverse-flow gradient density centrifuge without damaging the fluid. The particles can be provided to a patient in vivo or added to the fluid after it is removed from the patient. Some particles can carry and deliver oxygen and scavenge carbon dioxide. Other particles are conjugated to capture molecules for attaching to targets such as cancer cells, viruses, pathogens, toxins, or excess concentrations of a drug or element in the fluid. The targets are then removed from the fluid along with the particles by the aphaeresis instrument.

17 Claims, 11 Drawing Sheets

Related U.S. Application Data

(60) Provisional application No. 61/739,724, filed on Dec. 20, 2012, provisional application No. 61/729,948, filed on Nov. 26, 2012, provisional application No. 61/729,942, filed on Nov. 26, 2012, provisional application No. 61/671,682, filed on Jul. 14, 2012, provisional application No. 61/668,032, filed on Jul. 5, 2012.

(52) U.S. Cl.
CPC ........ *A61M 1/3679* (2013.01); *A61M 1/3687* (2013.01); *A61M 1/3696* (2014.02); *B01F 5/0602* (2013.01); *A61M 1/367* (2013.01); *A61M 2202/0433* (2013.01); *A61M 2206/11* (2013.01)

(58) Field of Classification Search
CPC ........ A61M 1/362; B04B 7/08; B01F 5/0602; B01F 5/0601; B01F 5/064; B01F 5/0646; B01J 19/2425
See application file for complete search history.

(56) References Cited

U.S. PATENT DOCUMENTS

| | | |
|---|---|---|
| 5,123,901 A | 6/1992 | Carew |
| 5,296,375 A | 3/1994 | Kricka |
| 5,386,734 A | 2/1995 | Pusinelli |
| 5,635,207 A | 6/1997 | Grinstaff et al. |
| 5,641,622 A | 6/1997 | Lake et al. |
| 5,663,051 A | 9/1997 | Vlasselaer |
| 5,679,394 A | 10/1997 | Long, Jr. et al. |
| 5,811,521 A | 9/1998 | Kluger et al. |
| 5,840,502 A | 11/1998 | Van Vlasselaer |
| 6,071,422 A | 6/2000 | Hlavinka et al. |
| 6,277,060 B1 | 8/2001 | Neumann |
| 6,280,375 B1 | 8/2001 | Meisberger et al. |
| 6,416,456 B2 | 7/2002 | Zanella et al. |
| 6,497,674 B1 | 12/2002 | Steele et al. |
| 7,297,272 B2 | 11/2007 | Min et al. |
| 7,531,133 B2 | 5/2009 | Hole |
| 2003/0026024 A1 | 2/2003 | Igarashi |
| 2003/0026855 A1 | 2/2003 | Kameneva et al. |
| 2003/0036518 A1 | 2/2003 | Samain et al. |
| 2003/0082795 A1 | 5/2003 | Shuler et al. |
| 2004/0102732 A1 | 5/2004 | Naghavi et al. |
| 2005/0016851 A1* | 1/2005 | Jensen ............... B01F 5/0646 204/471 |
| 2005/0087122 A1* | 4/2005 | Ismagliov ........... B01F 5/0646 117/2 |
| 2005/0129580 A1* | 6/2005 | Swinehart .......... B01F 5/0475 422/400 |
| 2006/0003439 A1 | 1/2006 | Ismagilov et al. |
| 2006/0240964 A1 | 10/2006 | Lolachi et al. |
| 2006/0280798 A1 | 12/2006 | Ensoli |
| 2007/0026024 A1 | 2/2007 | Drees |
| 2007/0258888 A1 | 11/2007 | Feldmann |
| 2009/0088679 A1 | 4/2009 | Wood et al. |
| 2009/0245017 A1* | 10/2009 | Paul .................... B01F 5/061 366/337 |
| 2010/0022680 A1* | 1/2010 | Karnik ............... A61K 47/6937 523/105 |
| 2010/0120132 A1* | 5/2010 | Koo ................ G01N 33/54333 435/287.2 |
| 2011/0056575 A1* | 3/2011 | Hong .................. B01F 5/0646 137/624.11 |
| 2011/0105982 A1* | 5/2011 | Leonard ............. A61M 1/3482 604/6.01 |
| 2011/0201986 A1 | 8/2011 | Howell et al. |
| 2011/0224645 A1 | 9/2011 | Winqvist et al. |
| 2012/0077662 A1 | 3/2012 | Ostafin et al. |
| 2012/0164231 A1 | 6/2012 | Ostafin et al. |
| 2014/0008301 A1 | 1/2014 | Ostafin et al. |
| 2015/0238432 A1 | 8/2015 | Ostafin et al. |
| 2015/0321204 A1 | 11/2015 | Ostafin et al. |

FOREIGN PATENT DOCUMENTS

| | | |
|---|---|---|
| CN | 101322029 | 12/2008 |
| EP | 0416575 | 3/1991 |
| WO | 1995/528915 | 11/1995 |
| WO | 1999/002269 | 1/1999 |
| WO | 2005/097208 | 10/2005 |
| WO | 2006/020100 | 2/2006 |
| WO | 2006/115938 | 11/2006 |
| WO | 2008/107167 | 9/2008 |
| WO | 2011/025755 | 3/2011 |
| WO | 2011/025756 | 3/2011 |
| WO | 2014/008490 | 1/2014 |

OTHER PUBLICATIONS

Baran, et al., "Detection of Cancer Cells in the Blood by FACS Sorting of CD45-Cells", Int. J. Mol. Med., vol. 1, No. 3, 1998, 573-581.

Beltinger, et al., "A Simple Combined Microdissection and Aspiration Device for the Rapid Procurement of Single Cells from Clinical Peripheral Blood Smears", Mol. Path., vol. 51, No. 4, 1998, 233-236.

Brandt, et al., "Two-Layer Buoyant Density Centrifugation Gradient for Enrichment of Prostate-Derived Cells and Cell Clusters from Peripheral Blood", Clinical Chemistry, vol. 42, No. 11, 1996, 1881-1882.

Brugger, et al., "Mobilization of Tumor Cells and Hematopoietic Progenitor Cells Into Peripheral Blook of Patients With Solid Tumors", Blood, vol. 83, No. 3, 1994, 636-640.

Buckner, et al., "Leukapheresis by Continuous Flow Centrifugation (CFC) in Patients with Chronic Myelocytic Leukemia (CML)", Blood, vol. 33, 1969, 353-369.

Campana, et al., "Detection of Minimal Residual Disease in Acute Leukemia: Methodologic Advances and Clinical Significance", Blood, vol. 85, No. 6, 1995, 1416-1434.

Chang, "Blood Substitutes Based on Nanobiotechnology", Trends in Biotechnology, vol. 24, No. 8, 2006, 372-377.

Denis, et al., "Detection of Disseminated Tumor Cells in Peripheral Blood of Colorectal Cancer Patients", Int J Cancer, vol. 74, No. 5, 1998, 540-544.

Glaves, et al., "Haematogenous Dissemination of Cells from Human Renal Adenocarcinomas", Br J Cancer, vol. 57, 1988, 32-35.

Harlozinska, et al., "Density Distribution, Cytomorphologic Features and Immunologic Characteristics of Ovarian and Endometrial Clear Cell Carcinomas", Acta Cytologica, vol. 34, No. 5, 1990, 657-663.

Henkel-Hanke, et al., "Artificial Oxygen Carriers: A Current Review", AANA Journal, vol. 75, No. 3, 2007, 205-211.

Hester, et al., "Principles of Blood Separation and Component Extraction in a Disposable Continuous-Flow Single-Stage Channel", Blood, vol. 54, No. 1, 1979, 254-268.

Hill, "Oxygen Therapeutics—Current Concepts", Canadian Journal of Anaesthesia, vol. 48, No. 4, 2001, S32-S40.

Jahr, "Blood Substitutes as Pharmacotherapies in Clinical Practice", Curr Opin Anaesthesiology, vol. 20, No. 4, 2007, 325-330.

Judson, et al., "Closed Continuous-Flow Centrifuge", Nature vol. 217, 1968, 816-818.

Kabalnov, et al., "Phospholipids as Emulsion Stabilizers. 1. Interfacial Tensions", Langmuir, vol. 11, No. 8, 1995, 2966-2974.

Karczewski, et al., "The Efficiency of an Autotransfusion System for Tumor Cell Removal from Blood Salvaded During Cancer Surgery", Anesth Analg, vol. 78, No. 6, 1994, 1131-1135.

Keipert, "OxygentTM, a Perfluorochemical-Based Oxygen Therapeutic for Surgical Patients", Blood Substitutes, Chapter 28, 2006, 312-323.

Kim, et al., "Artificial Oxygen Carriers as Red Blood Cell Substitutes: a Selected Review and Current Status", Artificial Organs, vol. 28, No. 9, 2004, 813-828.

(56) References Cited

OTHER PUBLICATIONS

Klein, et al., "Transperitoneal Oxygenation with Fluorocarbons", Anesthesia and Analgesia, vol. 65, No. 7, 1986, 734-738.
Koch, et al., "Duration of Red-Cell Storage and Complications after Cardiac Surgery", N Engl J Med, vol. 358, 2008, 1229-1239.
Ness, "Oxygen Therapeutics-Pursuit of an Alternative to the Donor Red Blood Cell", Arch Pathol Lab Med, vol. 131, No. 5, 2007, 734-741.
Ng, et al., "Buoyant Density of EMT6 Fibrosarcoma Cells", Cell Biophysics, vol. 2, No. 2, 1980, 153-163.
Racila, et al., "Detection and Characterization of Carcinoma Cells in the Blood", Proc Natl Acad Sci, vol. 95, No. 8, 1998, 4589-4594.
Sabile, "Efficiency of Ber-EP4 Antibody for Isolating Circulating Epithelial Tumor Cells Before TR-PCR Detection", Am J Clin Pathol, vol. 112, No. 2, 1999, 171-178.
Schmidt, "Calcium Phosphate Based Nanoshell for use in Biomedical Applications", University of Notre Dame Electronic Theses & Disertations, 2006, 1-347.
Suarez-Quian, "Laser Capture Microdissection of Single Cells from Complex Tissues", Biotechniques, vol. 26, No. 2, 1999, 328-335.
Thomas, et al., "Purification of Hematopoietic Stem Cells for Further Biological Study", Methods, vol. 17, No. 3, 1999, 202-218.

* cited by examiner

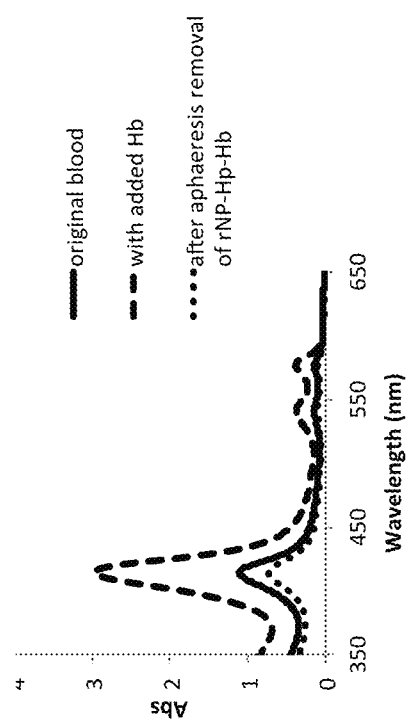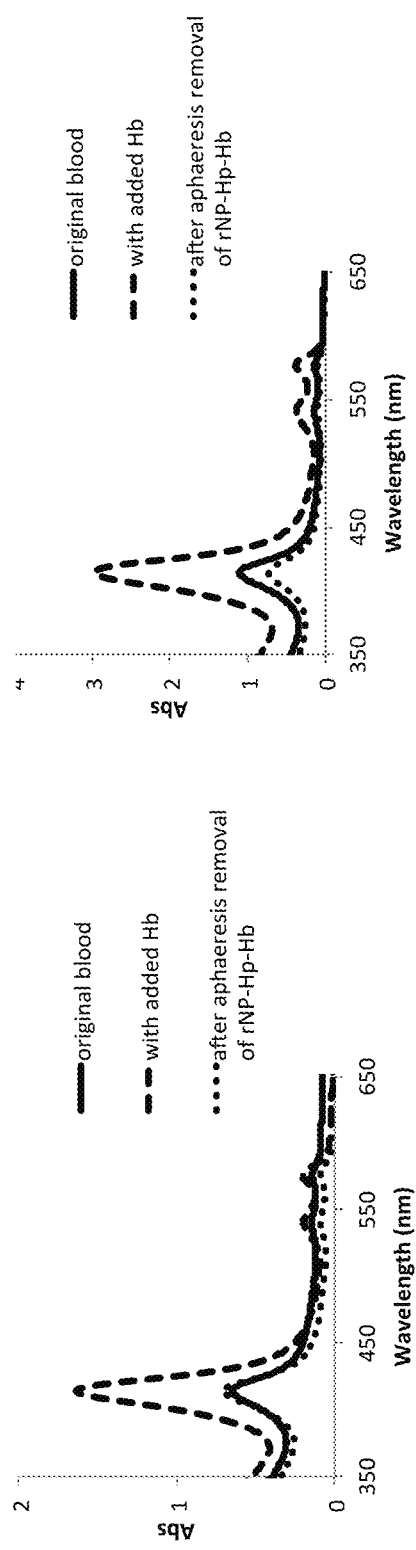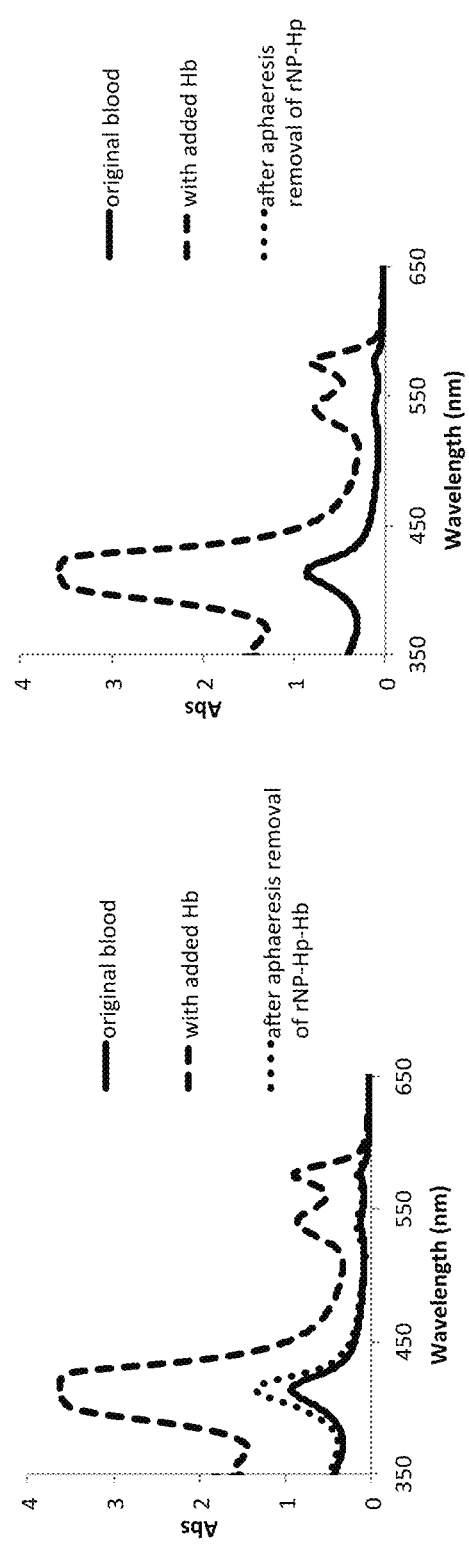

THERAPEUTIC RETRIEVAL OF TARGETS IN BIOLOGICAL FLUIDS

CROSS-REFERENCE TO RELATED APPLICATIONS

This application is a Continuation-In-Part of U.S. application Ser. No. 13/936,092 entitled Therapeutic Retrieval of Targets in Biological Fluids, filed Jul. 5, 2013 which claims priority to and the benefit of the filing of U.S. Provisional Patent Application Ser. No. 61/739,724, entitled "Therapeutic Reverse-Flow Density Gradient (RFDG) Aphaeresis", filed on Dec. 20, 2012; U.S. Provisional Patent Application Ser. No. 61/729,942, entitled "Retrieval of Iron and Other Divalent Metals in the Plasma with Reverse-Flow Density Gradient (RFDG) Centrifugation", filed on Nov. 26, 2012; U.S. Provisional Patent Application Ser. No. 61/729,948, entitled "Retrieval of Chemotherapeutic Agents and Metastatic Cancer Cells from Blood with Reverse-Flow Density Gradient (RFDG) Centrifugation", filed on Nov. 26, 2012; U.S. Provisional Patent Application Ser. No. 61/671,682, entitled "Retrieval Viruses in the Plasma with Reverse-Flow Density Gradient (RFDG) Centrifugation", filed on Jul. 14, 2012; and U.S. Provisional Patent Application Ser. No. 61/668,032, entitled "Retrieval of High-Density Particle Conjugated Hemoglobin in the Plasma with Reverse-Flow Density Gradient (RFDG) Centrifugation", filed on Jul. 5, 2012. The specification and claims of all of these applications are incorporated herein by reference.

This application is also related to U.S. patent application Ser. No. 13/322,757, entitled "Synthesis of Oxygen Carrying, Turbulence Resistant, High Density Submicron Particulates", which claims priority to PCT application Serial No. PCT/US10/46417, filed on Aug. 24, 2010, and U.S. patent application Ser. No. 13/322,790, entitled "Method and Apparatus for Continuous Removal of Submicron Sized Particles in a Closed Loop Liquid Flow System", which claims priority to PCT application Serial No. PCT/US2010/046421, filed on Aug. 24, 2010, both of which PCT applications claimed priority to and the benefit of the filing of U.S. Provisional Patent Application Ser. No. 61/236,810, filed on Aug. 25, 2009. The specifications and claims of all of these applications are incorporated herein by reference.

FEDERALLY SPONSORED RESEARCH OR DEVELOPMENT

The U.S. Government has a paid-up license in this invention and the right in limited circumstances to require the patent owner to license others on reasonable terms as provided for by the terms of Contract Nos. HHSN268201200059C and 3R41HL095250-01A1S1 awarded by the U.S. National Institutes of Health.

BACKGROUND OF THE INVENTION

Note that the following discussion refers to a number of publications and references. Discussion of such publications herein is given for more complete background of the scientific principles and is not to be construed as an admission that such publications are prior art for patentability determination purposes.

Many adverse health conditions result in the accumulation of abnormal compositions in the blood. For example, excess drugs given to patients, self consumed drugs and alcohol, and other consumables may be reflected in abnormal blood compositions. Some of the components found in the blood of affected individuals are used as diagnostic markers for disease and health conditions, while others may contribute to further problems by causing secondary symptoms and conditions. Medical treatment in such cases aim at reducing, masking or counteracting the effects of specific molecules and toxins, and supporting body processes that facilitate their clearance from the body. When symptoms become severe, the body can no longer handle the abnormal compositions, and facilitated medical intervention may be insufficient. Patients may suffer permanent damage or even death as a result.

Aphaeresis is a well-established clinical method that is used to separate components of blood for treatment or donation. In this method components of the blood which span a relatively narrow range of densities, but a much wider range of molecular weight and size, can be efficiently, rapidly, and continuously separated. Because blood is a heterogeneous non-ideal fluid, and most of the molecules and/or cells that are diagnostic for a disease fall within the density range spanned by the largest and smallest blood components, conventional aphaeresis is often ineffective or inefficient as an exclusive therapeutic device to collect and reduce the body's disease load, except possibly in cases where a major blood component is exchanged for a similar component obtained from healthy individuals (e.g. transfusion of red blood cells, harvesting of stem cells, platelets, white cells, removal of defective cells, etc.). Even some cells like metastatic cancer cells and stem cells are similar enough to normally present blood corpuscles to make separation difficult. Separation by aphaeresis is based on density and many undesirable components cannot be separated by density.

There are many situations where separation of targets from fluids is desirable. For example, patients with malignant cancer are typically treated with radiation and chemotherapeutic agents by scheduled infusion. Despite these efforts for many cancers the frequency of recurrence and metastasis remains significant. In some cases the cancer may be kept at bay if evidence for recurrence or continued malignancy could be caught early and the therapy modified appropriately. However, detecting evidence for metastatic cancer cells at early stages is difficult. By the time imaging and blood chemistry markers are able to reveal a problem the metastatic cancer is advanced and more aggressive treatment is required. Exacerbating this problem is the potential for some cancer cells to change their resistance to drug over time, which suggests that if effective detection and eradication could occur at early stages then patient prognosis could be significantly improved. Moreover, when present in sufficient quantity, certain cancer cells can be isolated from tissues such as blood and detected using immunological methods. Diagnosis therefore relies on the ability to find these diseased cells, which may be present in exceedingly small quantities.

Treatments of some viral diseases are available and preventable by immunization, but others are not. A patient who has not been immunized for a viral disease may be able to develop natural immunity and eventually build resistance to the disease. During this period, however, the patient may suffer from fever, infection and even life threatening symptoms, despite the intervention of indirect treatments to ease symptoms. Thus, being able to directly reduce the proliferation of viruses in the body of patients in crisis situations could bring significant benefits leading to recovery from viral diseases. In addition, it has become evident that methods to remove viruses (e.g., HIV, Ebola, or Hepatitis C) early in the infection greatly impacts prognosis and the effect of therapeutic treatments. Similarly, studies have shown that reducing the initial exposure load to toxins (e.g. snake bites, bacterial, or insect bites) can dramatically affect recovery, even avert death. Whether or not anti-toxin is available, by reducing the initial toxin load by removing toxins from the blood, neurotoxic, hemotoxic, necrotic, and other damage, as well as time spent in the hospital, may be minimized and disfigurement and death prevented.

Chelation therapeutics are drugs that are taken by patients exhibiting signs of excessively high metal levels such as iron. Taken by injection or orally these drugs supplement the transfusion therapy and prolong patient well-being and avoid crisis. Compliance with injection regimes has been difficult, but greatly improved with new oral medications. Bioavailability of oral drugs is still problematic and side effects arising from the larger than needed dosages that must be taken to reach consistent therapeutic levels is still an issue. The ability to lower iron levels in the blood could reduce side effects of transfusion therapy as well as alleviate the suffering of those with excess iron in the blood.

Patients with chronic hemoglobinopathies and other hemolytic diseases are typically treated by regular transfusion to replace lost oxygen carrying function and remove defective cells and their breakdown products. However, unlike the blood cells normally produced in the body, transfused blood cells are more fragile and tend to break down quicker in the blood stream. This leads to release of free iron from hemoglobin into the blood and eventual accumulation of iron in tissues and organs since the normal transferrin/ferritin network becomes overloaded and clearance of iron from the body cannot keep up. In those individual with defective iron clearance systems such as those with iron overload syndrome, the problem is even more acute.

In case of sickle cell anemia, the red blood cells (RBC) of patients are hemolyzed and the hemoglobin (HbS) released in the plasma become a cause of severe oxidative stress. Specifically, intravascular release of the tetrameric Hb results in its disassociation into a dimeric form. As a reactive molecule, hemoglobin can generate oxidant species. Outside a red blood cell, hemoglobin can react with plasma compounds, leading to oxidations. Free hemoglobin (Hb) is linked to the susceptibility of deoxyhemoglobin to oxidation, leading to the production of methemoglobin, which has a peroxidative activity and forms further reactive $O_2$ species. Oxidation of methemoglobin also releases hemin, which rapidly associates with membranes, leading to cytotoxicity. The Hb scavenger Haptoglobin (Hp) will irreversibly bind the dimeric form of Hb. The Hp-Hb complex can associate with the receptor CD163, found on the surface of monocytes and macrophages and then endocytosed for removal by degradation in the liver. However, when the binding capacity of Hp is overwhelmed, the hemoglobin (Hb) can reach and overload the absorptive capacity of the kidney (hemoglobinuria), leading to nephrotoxicity. Plasma free hemoglobin (PFH) is one of the causes of serious oxidative side effects in patients with sickle cell anemia (SCA). The PFH circulating in the blood damages the patient's tissues and organs.

Treatment of these diseases mostly relies on drugs, high energy radiation, temperature, immunity, etc., which usually take place while these pathogens still reside in the body of the patient, which causes unwanted side effects. Thus there is a need for a therapeutic method that removes those pathogens/unwanted molecules from the blood circulation of the patient.

Use of retrievable nanoparticles (rNP) functionalized with a capture molecule (rNP-capture molecule) capable of binding to a target of interest if present in solution is useful for removing molecules of interest from fluid especially biological fluid. Mechanical mixing of the solution containing the rNP-capture molecule and its target of interest decreases the segregation of the rNP-capture molecule and its target in solution and enhances the rate of binding of the rNP-capture molecule and target of interest by increasing the rate of random collision. Common mechanical mixing techniques to decrease segregation of molecules in solution include vortexing, tilt mixing, stirring with paddle or magnet, shaking solution with a shaker plate, and inversion mixing for example to induce turbulence. Turbulence may randomly increase the collision frequency between nanoparticles and molecules.

BRIEF DESCRIPTION OF THE INVENTION

One embodiment of the present invention provides an aphaeresis apparatus for removing from a flowing biological fluid high density nanoparticles functionalized with a capture molecule, the apparatus comprising a laminar flow mixing device comprising a plurality (n) of tubes with each tube of the plurality of tubes having an inner diameter of a2 which is between about 1-5 mm and a length of l2 which is between about 0.001-24 m through which each tube of the plurality of tubes permits stable laminar flow of the biological fluid at a flow rate of f2 and wherein the total flow rate of the biological fluid through the laminar flow mixing device is f2×n which is about equal to the total flow rate of the biological fluid entering the laminar flow mixing device from a first tube. The first tube has a diameter A1 through which the biological fluid flows at a flow rate F1 and wherein F1>f2 and wherein n×$a_2$ is about equal to A1. A second tube has an inner diameter A3 and is in fluid communication with the plurality of tubes of the laminar flow mixing device and is positioned at the exit of the plurality of tubes and connects the plurality of tubes of the laminar flow mixing device with a rotor of a reverse-flow density gradient (RFDG) centrifuge wherein the flow rate in the second tube is F3 is about equal to F1. The RFDG centrifuge rotor is capable of receiving the biological fluid mixed with the high density particles functionalized with the capture molecule and separating the high density particles functionalized with the capture molecule from less dense components of the biological fluid. The apparatus may further comprise a pump for pumping the biological fluid through said laminar flow mixing device and a syringe pump located before said laminar flow mixing device for combining said high density particles with the biological fluid. The centrifuge may comprise a variable element, said element selected from the group consisting of spin rate, number of open outlet ports, and flow rate of liquid through each outlet port. The position of the plurality of tubes may be substantially vertical or horizontal, in a preferred embodiment the plurality of tubes are positioned substantially in a horizontal position. The number of tubes of the plurality of tubes can be between about 2-64, 5-50, 10-40 or 20-35. In a preferred embodiment the biological fluid is blood. The apparatus accepts blood from a donor and returns the blood to the donor after aphaeresis treatment via aphaeresis tubing. The donor may be a human or animal in need of treatment. The apparatus has a total flow volume of the biological fluid of between 30-35 ml/min. A tube of the plurality of tubes is substantially straight but may have a curve which does not prevent laminar flow or a stable laminar flow within the tube. The first and/or the second tube is in fluid communication with the plurality of tubes of the laminar flow mixing device via an inlet/outlet connecting the plurality of tubes with the first and/or the second tube. The inlet/outlet can be shaped like a funnel with a wider portion of the funnel adjacent the laminar flow mixing device.

Another embodiment of the present invention is a laminar flow mixing device for mixing functionalized high density nanoparticles with molecules of interest in a fluid, the laminar flow mixing device comprising a plurality (n) of tubes arranged in parallel with each tube of the plurality of straight tubes having an inner diameter of a2 and a length of l2 through which each tube of the plurality of tubes flows the biological fluid at a volume flow rate of f2 and wherein the total flow rate of the biological fluid through the laminar flow mixing device is f2×n which is about equal to the total flow rate of the biological fluid entering the laminar flow mixing device from a first tube in fluid communication with the plurality of tubes of the laminar flow mixing device. The first tube has a diameter A1 through which the biological fluid flows at a flow rate F1 and wherein F1>f2 and wherein n×$a_2$ is about equal to A1. A second tube has an inner diameter A3 is attached to an outlet of the laminar flow mixing device to receive the biological fluid exiting the plurality of tubes of the laminar flow mixing device wherein the volume flow rate in the second tube is F3≈F1. The plurality of tubes is between 2-64, 5-50, 10-40 or 20-35 tubes. The length of the plurality of tubes of the laminar flow mixing device is between about 0.001-240 m. The plurality of tubes of the laminar flow mixing device and the first tube and/or the second tube are in fluid communication via a funnel inlet/oulet with a wider portion of the funnel adjacent the laminar flow mixing device. In one embodiment of the present invention there are no spiral elements in the mixing device and/or there is no mechanical stirring within the mixing device. The parallel tubes are arranged side by side.

Yet another embodiment of the present invention provides a method of mixing functionalized nanoparticles with a flowing fluid in a tube wherein the flowing fluid includes a target analyte, the method comprising introducing to the flowing fluid containing a target analyte a first solution containing functionalized nanoparticles having a capture molecule that specifically binds the target analyte. The flowing fluid with functionalized nanoparticles is passed a laminar flow mixing device via the tube, the laminar flow mixing device comprising a plurality (n) of tubes arranged in parallel with each tube of the plurality of tubes having an inner diameter of a2 and a length of l2 through which each tube of the plurality of tubes permits stable laminar flow of the biological fluid at a flow rate of f2 and wherein the total flow rate of the biological fluid through the laminar flow mixing device is f2×n which is about equal to the total flow rate of the biological fluid entering the laminar flow mixing device from the tube in fluid communication with the plurality of tubes of the laminar flow mixing device. The first tube having a diameter A1 through which the biological fluid flows at a volume flow rate F1 and wherein F1>f2 and wherein n×a2 is about equal to A1. Within the plurality of tubes of the laminar flow mixing device establishing a stable laminar flow of the fluid for a predetermined time period to allow coupling of the functionalized nanoparticle with the target analyte to produce a reaction rate that is faster than gentle end-to-end mixing of the reaction for the same time and concentrations of functionalized nanoparticle and the target analyte in solution.

Yet another embodiment of the present invention provides a method of removing plasma free hemoglobin from the flowing blood of a patient in need of treatment the method comprising adding to the extracorporeal flowing blood of the patient a retrievable nanoparticle functionalized with haptoglobin (rNP-Hp) that has a binding affinity for plasma free hemoglobin. The extracorporeal blood with the rNP-Hp is passed to an aphaeresis apparatus for removing from the flowing blood the rNP-Hp via a laminar flow mixing device comprising a plurality (n) of tubes with each tube of the plurality of tubes having an inner diameter of about 1-5 mm and a length of l2 which is between about 0.001-24 m through which each tube of the plurality of tubes permits stable laminar flow of the blood at a flow rate of f2 and wherein the total flow rate of the blood through the laminar flow mixing device is f2×n which is about equal to the total flow rate of the blood entering the laminar flow mixing device from a first tube. The first tube has a diameter A1 through which the blood flows at a flow rate F1 and wherein F1>f2 and wherein n×a2 is about equal to A1. A second tube has an inner diameter A3 and is in fluid communication with the plurality of tubes of the laminar flow mixing device and is positioned at the exit of the plurality of tubes and connects the plurality of tubes of the laminar flow mixing device with a rotor of a reverse-flow density gradient (RFDG) centrifuge wherein the flow rate in the second tube is F3 is about equal to F1. The RFDG centrifuge rotor is capable of receiving the blood mixed with the rNP-Hp and rNP-Hp-Hb and separating them from less dense components of the blood. The blood without the rNP-Hp or rNP-Hp-Hb is returned to the patient with less plasma free hemoglobin than the amount of plasma free hemoglobin in the blood prior to treatment. The donor may be an infant, child, or adult human or animal of any size that is in need of treatment. In a preferred embodiment, the laminar flow mixing device has a total flow rate of the blood of between 20 to 40 ml/min with a flow rate within a single tube of the plurality of tubes of the laminar flow mixing device of between about 0.5-3 ml/min and provides a residence time of blood within the laminar flow mixing device of about 0.5-5 min.

One aspect of the present invention provides for an apparatus for mixing nanoparticles functionalized with a capture molecule with a solution having a molecule of interest that is the "target" of the capture molecule wherein the apparatus for mixing enhance the rate of capture molecule and target binding in solution as compared to the same reaction in a closed container with end-to-end mixing for the same period of time.

Another aspect of the present invention is to provide a method of enhancing the rate of capture molecule and target binding in solution when the solution transits through a tube that promotes laminar flow.

Another aspect of the present invention is a laminar flow reaction device for enhancing the rate of binding of capture molecule on a nanoparticle with its target in the presence of laminar flow and with less turbulence than occurs with mechanical mixing which will cause lysis of red blood cells when the fluid is blood.

One aspect of one embodiment of the present invention is to provide a method of removing nanoparticle bound molecules from blood of a patient during aphaeresis.

Another aspect of one embodiment of the present invention is to provide a mixing chamber for mixing a capture particle with blood of a patient during aphaeresis. For example, the mixing chamber is positioned along the aphaeresis loop.

One aspect of one embodiment of the present invention provides for increasing the removal of molecules within the blood during aphaeresis with a mixing device as compared to the removal of molecules within the blood during aphaeresis without the mixing device.

Another aspect of an embodiment of the present invention is to remove molecules within the blood during aphaeresis while not increasing hemolysis of the blood beyond the amount that occurs during aphaeresis in the absence of a laminar flood mixing device as disclosed herein.

Embodiments of the present invention are related to retrievable nanoparticles that can be mixed with a patient's blood and that are capable of selectively binding to target molecules, ions, viruses and/or cells to form a complex and the removal of the complex from the blood of a patient. Other embodiments of the present invention are related to a low-cost, continuous reverse-flow density gradient centrifuge (RFDGC) that can perform this retrieval, either extracorporeally or corporeally, optionally comprising an efficient continuous mixing device for mixing the retrievable nanoparticles and the target pathogens in the patient's blood without damaging other blood components. Further still a mixing apparatus to enhance binding of a functionalized nanoparticle and target of interest during transfusion is disclosed.

It is thus possible with embodiments of the present invention to therapeutically treat patients while minimizing side effects resulting from, for example, toxic substances, unmetabolized drugs, overdosed or unused drugs and particles such as imaging or carrier particles are removed from the bloodstream before they can become the secondary cause of toxins or disease. Additionally, embodiments of the present invention can be utilized to harvest high value proteins, peptides, cells, DNA, RNA, exosomes and circulating tumor cells (CTCs) from the biological fluids.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate an embodiment of the present invention and, together with the description, serve to explain the principles of the invention. The drawings are only for the purpose of illustrating various embodiments of the invention and are not to be construed as limiting the invention. In the drawings:

FIG. 14 A-D is a graph showing typical results of Hb capture by rNP-Hp in the LFRD during aphaeresis in two (2) animals that had different levels of unwanted Hb in their plasma.

Figure 1:
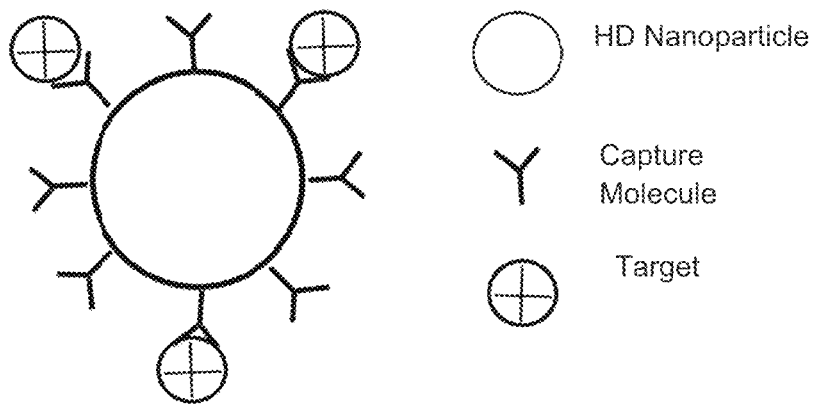
FIG. 1 is a schematic of an embodiment of a high-density particle of the present invention.

Further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

As used herein, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

As used throughout the specification and claims, the terms "capture molecule" or "target specific ligand" or "TSL" mean any moiety that selectively binds to both a target and embodiments of submicron particles of the present invention, including but not limited to ion, metal, chelator, lectin, haptoglobin, aptamer, DNA, nucleic acid fragment or sequence, ligand, antigen, antibody, protein nucleic acid, enzyme, macrophage, chemotherapy reagent, and the like. A capture molecule may also be any natural, synthetic or recombinant protein, fragment, sequence or molecule which, when attached to a high-density submicron particle retains its ability to form a stable complex with a desired target. As used throughout the specification and claims, the term "target" means a specific molecule, drug, cell fragment, cell, pathogen, toxin, poison, DNA, nucleic acid, nucleic acid fragment or sequence, peptide, antibody, antibody fragment, protein, polysaccharide, divalent metal, virus, fungus, bacterium, mycoplasm, and the like, typically associated with a disease or combination of diseases, or the equivalent thereof.

Embodiments of the present invention comprise high-density particles that can be delivered into a biological fluid either in vivo or extra-corporeally, and which are retrievable by aphaeresis methods. One embodiment comprises a PFC-containing emulsion, which comprises perfluorocarbon, for example perfluoroctanylbromide (PFOB), core surrounded by surfactant. The surfactant preferably comprises a phospholipid-based monolayer. The major surfactant in the monolayer typically comprises a monounsaturated neutral phospholipid, such as 18:1 (Δ9-Cis) PC (DOPC), which is 1,2-dioleoyl-sn-glycero-3-phosphocholine, but may alternatively comprise a monounsaturated negative headgroup phospholipid such as 18:1 (Δ9-Cis) PA (DOPA) which is 1,2-dioleoyl-sn-glycero-3-phosphate. The monolayer preferably also comprises PEGylated phospholipid to stabilize the structure, prevent aggregation, and offer stealth by preventing opsonization and adherence to cells, thereby increasing circulation half-life. The PEGylated phospholipid typically comprises approximately 10-40 PEG subunits and a PEGylated 18:1 DOPE derivative, for example 18:1 PEG1000 PE which is 1,2-dioleoyl-sn-glycero-3-phosphoethanolamine-N-[methoxy(polyethylene glycol)-1000], in which case the PEG portion comprises 22 subunits.

In some embodiments where attaching the high density particle to a target is desired, the monolayer will also preferably comprise a DOPE derivative with an extended headgroup terminating in a carboxyl or amine group used to conjugate the desired target specific ligand (TSL). In some embodiments the derivative comprises an 18:1 Dodecanyl PE which is 1,2-dioleoyl-sn-glycero-3-phosphoethanolamine-N-(dodecanyl) (DD-DOPE). The headgroup on DD-DOPE has an extension of approximately 2.3 nm ending in a carboxyl group. An antibody or other desired TSL can be covalently attached, for example using 1-Ethyl-3-[3-dimethylaminopropyl]carbodiimide hydrochloride (EDC) and Sulfo-(N-hydroxysulfosuccinimide) (S—NHS) chemistry. The final product typically has a diameter between 200-300 nm, which can be determined by, for example, dynamic light scattering (DLS). The PFC core typically is from approximately 4-20% by volume, the total surfactant is from approximately 0.2-1.5% by weight. Within this surfactant composition by molar %, for example, the major surfactant (DOPC or DOPA), the DD-DOPE, and the PEGylated phospholipid preferably range from approximately 85-90%, 8-10% and 4-5% respectively. The major volume typically comprises phosphate-buffered saline (PBS) or normal saline (0.9% NaCl).

Other embodiments of the high density particles comprise a solid core preferably comprising one or more nanoparticles such as 100 nm spheres comprising gold, titanium, silver, iron, silica, or a ceramic. The core is then surface modified, for example with ~5000 MW Thiol-PEG-COOH or HO-PEG-NH$_2$ groups.

An embodiment of the invention is submicron high-density particles as described above able to bind to a specific target in the blood or in another ideal or non-ideal fluid, including biological fluids such as, but not limited to, blood, plasma, urine or cell lysates, thereby forming the complex rHDP-X, where X specifies the target or in some cases (such as haptoglobin) an intermediary that attaches to the particles and also attaches to the target.

A more generalized version of this complex is shown in FIG. 1. The use of retrievable high-density particles (rHDP) accentuates the slight difference in density between some targets, such as cancer cells, and normal healthy cells, which facilitates retrieval of very small quantities or concentrations of targets from blood or other biological fluid, preferably using aphaeresis and reverse-flow density gradient centrifugation. The core is preferably covalently bonded to capture molecules using conventional cross-linking chemistries. The rHDP may be a nanoparticle ranging in size from 10-1000 nm. A rHDP is designed so that the rHDP has the highest density as compared to the other components in the solution to which is added rHDP. For example a rHDP is made more dense than any component that normally exists in blood such that rHDP can be separated from the other components of blood with an aphaeresis rotor of an aphaeresis system. A rNP can be isolated based upon density or other characteristic such as magnetic features. Once the functionalized rNPs are in contact with a patient's blood they will bind to their intended targets, for example via binding receptors or other markers on the surface of the targets. Multiple types of rHDP-X may be used as a cocktail formulated for specific and simultaneous removal of different targets associated with a disease or diseases, such as those often afflicting immuno-compromised patients. Some examples of high density particles that are unconjugated or conjugated to form the rHDP-X complex are listed in Table 1.

TABLE 1

| X | core | Layer 1 major components | Layer 1 minor components | Crosslinking | Other molecules | Primary target (e.g.) | Uses |
|---|---|---|---|---|---|---|---|
| none | PFOB PFD | DOPC (DOPA) | PEG-containing lipid | EDC/S-NHS or other | none | Dissolved gase | O$_2$ delivery/ CO$_2$ scavenger |
| anti-haptoglobin | PFOB PFD | DOPC (DOPA) | PEG-containing lipid | EDC/S-NHS or other | Anti-haptoglobin | haptoglobin | research |
| haptoglobin | Same | Same | Same | Same | haptoglobin | hemoglobin | SCD |
| Chelator | Same | Same | Same | Same | desferox-amine or similar | Iron | Therapeutic scavenger |
| lectin | Same | Same | Same | Same | Lectin | Fungus, toxins, carbohydrate | Therapeutic scavenger |
| other | Same | Same | Same | Same | Various | Virus, chemo-theraputics, cells toxins | Therapeutic scavenger |

The rHDP-X is retrieved or removed from the patient's blood, preferably using an aphaeresis system comprising reverse-flow density gradient (RFDG) aphaeresis cell-sorter, such as that disclosed in U.S. patent application Ser. No.

13/322,790. Some embodiments of the system may be portable and battery and/or solar powered, enabling use in locations where there is minimal technological infrastructure. In one embodiment, shown in FIG. 2, the particles are introduced into the patient's blood, such as via intravenous injection, for therapeutic purposes such as a chemotherapy infusion or to capture targets. The blood/particle mixture is pumped via pump 10 to reverse flow density gradient cell sorter 20, which separates out the particles and returns blood to the patient without the particles or targets, and preferably without damage to the blood or healthy blood cells. In another embodiment, shown in FIG. 3, the patient's blood is pumped via pump into mixing chamber, where particles are mixed with the patient's blood extra-corporeally, preferably at the inlet of the aphaeresis instrument (reverse flow density gradient cell sorter), which removes the conjugated particles and returns the blood to the patient. In this embodiment the particles never enter the patient's body. A pump may be located before or after RFDG cell sorter or RFDG cell sorter, respectively. In one example, the blood from a patient is continuously withdrawn and quickly mixed with the high-density retrievable nanoparticles activated with haptoglobin (rNP-HP). The aphaeresis instrument captures rNP-HP-HbS and discards it while cleaned blood returns to the patient and unreacted rNP-Hp recycles to the mixer for another round of capturing PFH. The pathway through which the blood travels outside the body during aphaeresis is known as the "aphaeresis loop".

Figure 3:
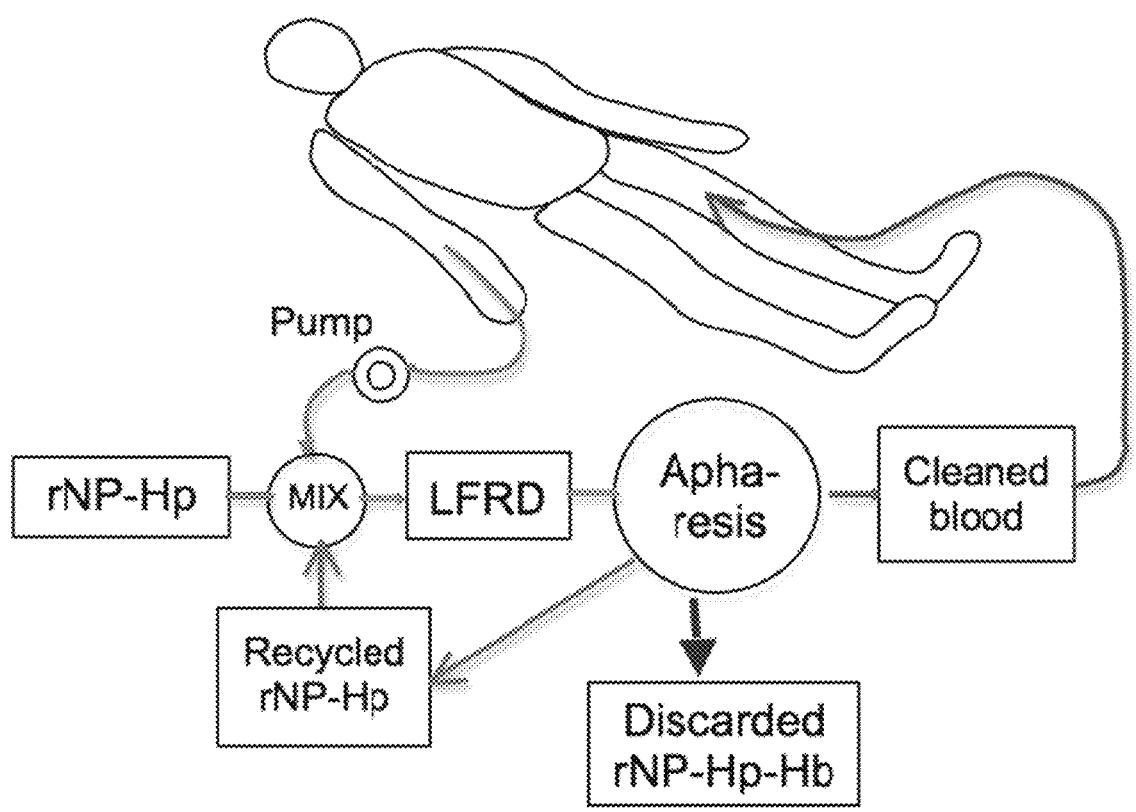
FIG. 3 is a schematic diagram showing extra-corporeal retrieval of high-density submicron particles in the blood in accordance with embodiments of the present invention. In this arrangement, the high density submicron particles do not enter the patient's body.

As shown in FIG. 3, aphaeresis with an extra-corporeal mixing chamber preferably utilizes a mixing chamber that facilitates the activated high-density nanoparticles binding to the targets without damaging blood components, especially the red blood cells, white cells and proteins. The process occurs within the range of volume and liquid flow rate acceptable to the reverse flow density gradient centrifuge (RFDGC). In this embodiment rNP are introduced to the blood extracorporeally. The blood is returned to the patient after all or substantially all of the rNP have been removed from the blood.

Figure 2:
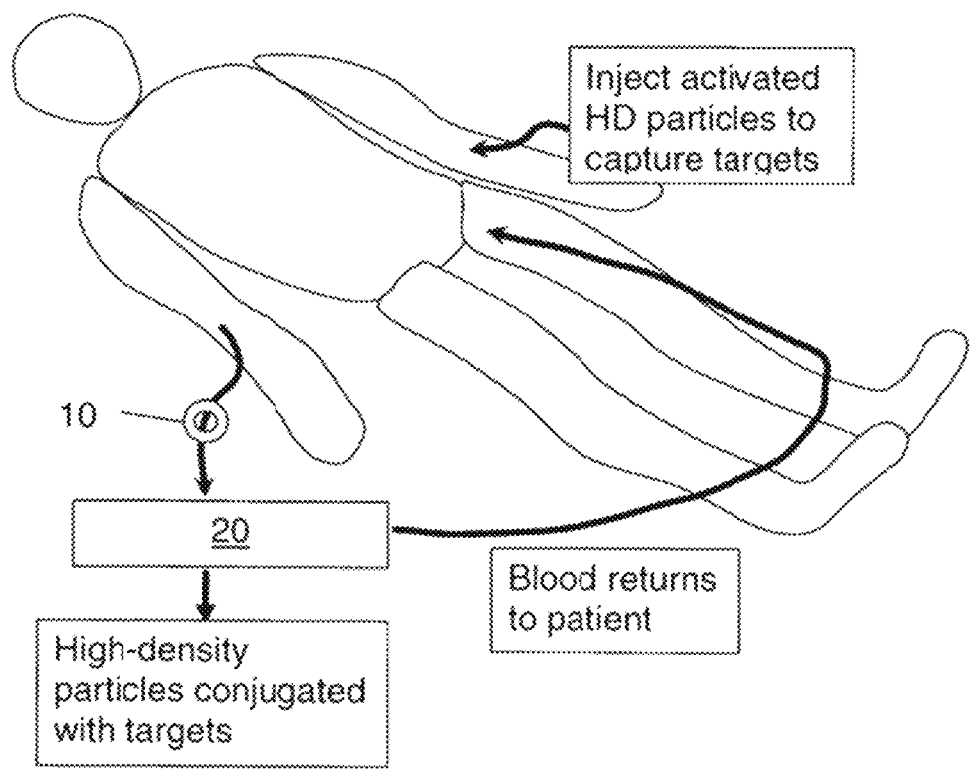
FIG. 2 is a schematic diagram showing corporeal introduction of targets conjugated with high-density submicron particles in the blood with a reverse flow density gradient (RFDG) aphaeresis system in accordance with an embodiment of the present invention.

One embodiment of the invention may be used to remove hemoglobin from plasma. The level of hemoglobin in blood plasma is known to increase among patients with hemolytic anemia, sickle cell anemia, thalassemia etc. Furthermore, chronic blood transfusion to these patients could further increase the level of free hemoglobin in the blood, and they may suffer from oxidative stress. Particles of the present invention can bind a large number of hemoglobin molecules (Hb), such as hemoglobin HbA, hemoglobin HbS, etc. One embodiment is to attach capture molecules like haptoglobin (Hp) or similar molecules to the high density submicron particles which then bind to Hb. Another embodiment is to attach anti-haptoglobin antibodies to the high density submicron particles that then binds Hp. And Hb in two steps or Hp-Hb complexes in one step. In this embodiment Hb is the target, and the particles form a complex with Hp (rHDP-Hp). Hp in plasma or on the nanoparticles captures from the plasma, forming rHDP-Hp-Hb due to the high affinity of Hp to Hb. In plasma, the Hp irreversibly binds Hb with high affinity ($K_d \sim 10^{-15}$ M) and fast rate constant ($\sim 5.5 \times 10^5$ $M^{-1}s^{-1}$). The rHDP-Hp may be injected intravenously into circulating blood, as shown in FIG. 2, or extracorporeally, as shown in FIG. 3. The haptoglobin preferably comprises human haptoglobin, preferably Haptoglobin 1-1, or at minimum its active binding region. This therapy will be useful to treat patients with excess Hb levels such as occurs in sickle cell anemia, Thalassemia, other anemic diseases, certain bacterial infections, certain snake-bites or drugs, or those undergoing surgery or suffering from injuries.

Adjustment of the size and surface properties of the rHDP-X complexes, and/or use of PEGylated and/or neutral lipids, ensures that the particles will make minimal contact with non-target blood components, bone marrow, the liver, or any other organs, thus minimizing or preventing opsonization and adherence to cells, thereby enhancing circulation half-life and limiting toxicity. Residence or mixing time of the rHDP-X with blood can be dynamically adjusted in the aphaeresis unit to maximize capture and recovery. The retrieval efficiency preferably self-adjusts by automatically recording the remaining content of the target material in the blood or other fluid.

Other embodiments of the present invention utilize some embodiments of rHDP-X for targeting and other embodiments of rHDP-X for drug delivery to form a theranostic cocktail. For example, such a cocktail could be used for the simultaneous delivery of chemotherapeutic or photodynamic therapy agents in addition to the capture and retrieval of cancer cells from blood. The nanoparticles may also carry chemotherapeutic, photodynamic or other therapeutics, and/or radiographic or MRI imaging molecules or substances in order to perform multiple functions, including, for example, particle tracking, thus enabling improved diagnosis monitoring of the effectiveness of treatment of the disease.

One or more embodiments of the present invention can improve a patient's health status in measurable ways in cases where one or multiple disease states coexist for which removal of metabolic reaction products, defective proteins or polysaccharides and other toxic or irritating substances leads to amelioration or symptoms and lessening of the toxic load on the immune, renal or hepatic systems. In addition to removing difficult to clear metabolic by-products of drugs, embodiments of the present invention may be used to treat and diagnose or prognose various types of cancers, viral infections, fungal infections, or bacterial infections, to reduce side effects of chemotherapy, and to reduce the level of toxins, alcohol and drugs in the blood. In some embodiments patients may be treated with high drug doses while minimizing side effects resulting from metabolized drugs, since unused or residual drugs and particles are preferably removed from the bloodstream.

Scavenging of Hb Using rNP-Hp and MB-Hp

To test Hb scavenging, normal human plasma from a blood bank was spiked with different amounts of Hb (0.4-2.0 nmol) from hemolyzed red blood cells (RBC) to simulate the slightly hemolyzed blood of patients with sickle cell anemia (SCA). An accepted Hb detection assay was utilized which exhibits good sensitivity. We were unable to detect hemoglobin in the normal plasma obtained from a healthy donor, but detected Hb in the spiked samples as low as 1 µM. In this experiment, 250 µl of preps (Hp-rNP) using DOPC as the primary surfactant and Hp conjugated to the surface via a carboxy-terminal DOPE-derivative (DD-DOPE) with and without added PEGylation were used. Additionally, a preparation involving Hp conjugated to an activated NHS-Magnetic Bead (MB) was run alongside these preps. Hemoglobin was added to the test formulations and incubated for 30 min at room temperature by end-end mixing using a tube rotator. The rNP-Hp preps were then centrifuged at 16K×15 min to collect the supernatants. The MB-Hp preparation supernatants were collected using a magnetic stand. These supernatants were tested for free (unbound) Hb. Table 2 is a summary of the results, which suggest: (a) both rNP preparation and MB scavenge Hb; (b) the stoichiometry of Hb:Hp for the rNP preps appears to be approximately 1:2, which implies that (i) 50% of the bound Hp is conjugated at a crucial domain on Hp required for Hb capture, or (ii) 50% of the Hp is sterically hindered/blocked and inaccessible to Hb, or (iii) 50% of the Hb may be non-dimeric; c) PEGylation does not affect the ability of Hp to bind Hb; and d) the Hp-MB complex is less efficient at scavenging Hb than the rNP-Hp formulation.

TABLE 2

| | Prep | | | | | | | | |
|---|---|---|---|---|---|---|---|---|---|
| | Prep without PEG9 | | | Prep With PEG9 | | | Prep With NHS-MB | | |
| | Hp/250 ul (nmol) | | | | | | | | |
| | 1.9 | | | 1.9 | | | 0.6 | | |
| Hb added (nmol) | 0.4 | 0.5 | 2.0 | 0.4 | 0.5 | 2.0 | 0.4 | 0.5 | 2.0 |
| Hb unbound (nmol) | 0 | 0 | 0.9 | 0 | 0 | 1.1 | 0 | 0 | 1.7 |
| Hb bound (nmol) | 0.4 | 0.5 | 1.1 | 0.4 | 0.5 | 0.9 | 0.4 | 0.5 | 0.3 |
| Hb bound (%) | 100 | 100 | 55 | 100 | 100 | 45 | 100 | 100 | 15 |

High-Density Particles May be Retrieved Up to 100% with an Aphaeresis Instrument High-density Magnetic Beads (Sera-Bind Speed Beads, Thermo Scientific, Freemont, Calif.) (MB) (2 g/ml, diameter=1.3 µm) were used to demonstrate their retrieval with the Cobe Spectra Aphaerseis System. The Cobe Spectra has a blood inlet and anticoagulant inlet ports. It also has three outlet ports, which recover the blood separated in the highest, middle and lowest densities. The ports are intended for RBC, buffy coat, and plasma. The middle port was closed and pH 7.4 buffered saline (PBS) was supplied through the anticoagulant port. MB (256 mg) were washed in PBS and suspended in PBS at a final volume of 500 ml. The weight of MB was determined after collecting them magnetically in an aliquot of suspension, removing the liquid and weighing the MB. Before aphaeresis, a 25 ml aliquot of the MB/PBS solution gave a reference MB weight of 12.7 mg. The aphaeresis instrument was primed with PBS as usual and the flow rate of the inlet was adjusted at 32.1 ml/min and that of anticoagulant 4.6 ml/min when needed. The aphaeresis instrument was prepared to collect samples from only the plasma port (low density) and RBC port (high density). The flow rates of the two exit ports were set at 19.2 and 17.5 ml/min, respectively. The third middle density port to collect white cells and platelets was sealed. The aphaeresis was repeated three times at different speeds of centrifugation, i.e. 500, 1,000 and 2,400 rpm. Each time, 25 ml was collected from each port. The amount of MB present in the effluent collected from each of the two ports was harvested magnetically, the fluid removed and the MB weighed. The % of separation of MB from the two ports at three different spin speeds is described in Table 3. The results demonstrate that at the total flow rate of 36.7 ml/min, a complete separation of MB can be achieved at 2,400 rpm. Although the conditions for separation of MB and its equivalent in the plasma and blood will be different, the results strongly suggest a complete isolation of high-density nanoparticles will be feasible by adjusting the spin speed of the aphaeresis instrument and the flow rates of liquid through each port.

TABLE 3

| Spin speed rpm | Plasma port mg | RBC port mg | Plasma port Wt % | RBC port Wt % |
|---|---|---|---|---|
| 2400 | 0.0 | 12.8 | 0.0 | 100.0 |
| 1000 | 2.4 | 10.2 | 19.0 | 81.0 |
| 500 | 6.0 | 7.2 | 45.5 | 54.5 |

The Efficient Conjugation of Haptoglobin onto rNP and Gold Submicron Particles

Hp-rNP were formulated using 2.6 mmol 1,2-dioleoyl-sn-glycero-3-phosphocholine (DOPC), 260 µmol 1,2-dioleoyl-sn-glycero-3-phosphoethanolamine-N-(dodecanyl) (DD-DOPE), 130 µmol 1,2-dioleoyl-sn-glycero-3-phosphoethanolamine-N-[methoxy(polyethylene glycol)-1000], 20% Vol perfluoroctanylbromide (PFOB) and 80% Vol PBS. The lipids (in chloroform) were mixed, rotovapped to dryness and vacuum dessicated for 3 days. They were reconstituted in 120 ml PBS. PFOB (30 ml) was added and the mixture emulsified (5000 rpm) for 1 minute to form uniform emulsion. The emulsion was homogenized at 30K×psi×10 passes to form 234 nm particles. Hp was conjugated using EDS/S—NHS chemistry and after centrifugation the supernatant was extensively dialyzed and the free Hp determined to calculate the amount bound.

Gold nanoparticles (100 nm) were complexed with Thiol-PEG-COOH (MW 5000) overnight, then conjugated with Hp using EDC/S—NHS chemistry. The particles were pelleted at 3K×g×15 min and the supernatant collected, dialyzed and free Hp determined as above. The results for both types of particles indicate efficient Hp conjugation. Greater than 82% Hp bound to the rNP's resulting in approximately 8 nmol Hp/ml of formulation, and greater than 51% Hp bound to the gold nanoparticles, resulting in approximately 2.3 nmol Hp/ml of formulation.

One embodiment of the present invention provides for a retrievable nanoparticle bound to haptoglobin (rNP-Hp) and a method to treat a patient with a depletion of CD163 macrophages resulting from SCA as compare to the population of CD163 in a patient without SCA and using the rNP-Hp to capture the sickle cell Hemoglobin (HbS) in the blood of SCA patients in need of therapy.

The rate of binding of plasma free HbS in solution with rNP-Hp, may be useful to retrieve a rNP-Hp-Hb complex extracorporeally during an aphaeresis treatment using an aphaeresis instrument connected to the continuous blood flow of the patient. Typically for a 150 lb male patient undergoing aphaeresis about 300 ml of blood is circulated outside of the body for treatment. Typically the 300 ml of blood is treated during aphaeresis in about 15 min. at the flow rate of about 32-33 ml/min. However, for patients with smaller blood volumes the amount of blood outside of the body will be less and the flow rate lower. For the example using a 150 lb male patient, the aphaeresis rotor contains about 280 ml of blood with the entrance of the extracorporeal tubing being about 3 mm ID and having this ID along its length and holding about 20 ml of blood in its length leading to the aphaeresis rotor. Typically prior to entering the aphaeresis rotor, blood leaves the patient and flows in a tube leading to the aphaeresis rotor for about 5 min. According to one embodiment of the present invention functionalized nanoparticles are introduced into the blood when the blood contains unwanted molecules. The introduction could begin immediately after the blood leaves the patient and prior to entering into the aphaeresis tube leading to the aphaeresis system or at any time during the transit of the blood from the body to the aphaeresis rotor. Residence time of the reactants in the aphaeresis loop is about 15 min. The aphaeresis loop includes the intravenous tube that carries blood to the rotor and the intravenous tube that carries blood back to the patient from the rotor. The aphaeresis loop may also include a laminar flow reaction device according to one embodiment of the present invention. The efficiency of the rNP functionalized with a capture molecule that captures a target in the blood (reaction) may be measured for example, at the exit port of the aphaeresis system. For example the measurement could be for the level of hemoglobin remaining in the blood returning to the patient after the treatment of the blood with rNP-Hp when the rNP is a HDP. In general, the rates of molecular interactions in plasma are sufficiently fast to maintain biochemical reactions when the reaction takes place in a closed system and there is sufficient mixing The examples of emulsifiers suitable for use include DOPC (1,2-dioleoyl-sn-glycero-3-phosphocholine), DD-DOPE (1,2-dioleoyl-sn-glycero-3-phosphoethanolamine-N-(dodecanyl)) and PEG-PL: 16-subunit (1,2-dioleoyl-sn-glycero-3-phosphoethanolamine-N-[methoxy(polyethylene glycol)-750]) and 22-subunit (1,2-dioleoyl-sn-glycero-3-phosphoethanolamine-N-[methoxy(polyethylene glycol)-1000]) but are not limited thereto. The nanoparticles are typically made according to the following example: surfactants are mixed, rotovaped and vacuum dessicated. The surfactants are reconstituted in PBS followed by addition of perfluorocarbon. This mixture is emulsified for 1 min at 5,000 rpm and results in a very uniform emulsion, which can then be homogenized at 30K×psi×10 passes. The result is a consistent, stable emulsion (200-300 nm mean diameter). These rNP's are then conjugated with human Hp1-1 using EDC/S—NHS chemistry, unreacted groups quenched and the preparation washed with PBS to remove any residuals. Large volumes can be washed and concentrated using our tangential flow filtration (TFF) system. The product can be autoclaved and after storage at room temperature has demonstrated stable size and zeta potential. No significant changes in size (<~15%) or zeta potential (no change) are seen after autoclaving and storage at room temperature for over 12 weeks.

To capture plasma free Hb and remove it from the blood with aphaeresis, rNP needs to be bound with Hp forming high density rNP-Hp, which in turn binds Hb. Formation of an amide linkage between Hp and the DD-DOPE moiety on the rNP surface results in cross linking of Hp to rNP. This is facilitated using 1-ethyl-3-[3-dimethylaminopropyl]carbodiimide hydrochloride (EDC) and N-hydroxysulfosuccinimide (S—NHS) in 2-(N-morpholino) ethane sulfonic acid (MES) buffer, pH 5.5. The following is a recipe for the synthesis of 2 ml rNP-Hp at room temperature. Mix 2 ml rNP+2 ml MES (50 mM, pH 5.5). Then add 0.2 ml each of EDC/MES and S—NHS/MES for a final concentration of EDC (5 mM), and S—NHS (10 mM). Mix for 2 min. Add 2 ml Na Borate (50 mM, pH 8.5), and add Haptoglobin (Athens Research) in PBS (at ~1 mg Hp/ml rNP) and rotate for 2 hr for end to end mixing. Gently pellet by centrifugation, collect supernatant and dialyze×3 exchanges with PBS (Sample: PBS>1:250) and then the dialyzed supernatant is used to determine the unbound amount of Hp. Resuspend pellet in 1 ml Tris (10 mM, pH 7.5) for 1 hr (Tris is used to block unreacted S—NHS). Wash 3 times with 3 ml PBS and adjust the final total volume to 2 ml with PBS; store at 4° C. The amount of Hp conjugated is determined spectrophotometrically with the difference in amount added vs. that found in the supernatant.

Pegylation is a commonly used procedure to enhance particle stealth by reducing the occurrence of osponization and agglomeration while enhancing solubility in buffer and serum (Jokerst et al., Nanomedicine 2011 6:715-728). The effect of increasing degrees of pegylation of the rNP (3-5 mol % of total surfactant) on the ability to bind haptoglobin was investigated. Pegylation at 5 mol % of total surfactant resulted in poor conjugation of Hp (data not shown) most likely due to increased steric hindrance. Pegylation at 3 mol % of total surfactant was used to produce rNP-Hp1-1, and those results were found reproducible. Alternative cross linker to EDC/S—NHS 1-ethyl-3-[3-dimethylaminopropyl] carbodiimide hydrochloride (EDC) and N-hydroxysulfosuccinimide is (sulfosuccinimydyl) suberate (BS3)

The binding of two different types of Hp's, i.e. Hp1-1 and Hpmix (unknown mixing proportions by Athens of Hp1-1, Hp2-1, Hp2-2) to two different types of rNP, i.e. the emulsions having 16 subunit PEG (PEG16) and 22 subunit PEG (PEG22) was compared. In other words, there will be 4 different types of cross-linking as shown in Table 4 and they are identified as A, B, C, and D. The amount of rNP-Hp cross linking formation was estimated in PBS spectrophotometrically. Before mixing of rNP and Hp, the concentration of Hp was estimated at 280 nm. After mixing the two components for at least 1 hr, the complex was removed centrifugally and the concentration of Hp in the supernatant was again estimated spectrophotometrically to yield the unbound concentration of Hp. The difference between the two measurements was assumed to be the bound concentration of Hp and results are shown in Table 4 Hp1-1 is less efficiently bound to rNp than is Hpmix to rNp. Two different types of Hp were cross-linked over rNP having two different emulsifiers and shown as A, B, C and D. Significantly different binding efficiency between Hp1-1 and Hpmix was found.

TABLE 4

| Types | Hp Form | PEG form in rNP | Hp added (μg/ml) | Hp bound (μg/ml) | Hp bound (%) |
| --- | --- | --- | --- | --- | --- |
| A | Hp1-1 | 16 Subunits | 960 | 269 | 28 |
| B | Hp1-1 | 22 Subunits | 807 | 226 | 28 |
| C | Hpmix | 16 Subunits | 1089 | 501 | 46 |
| D | Hpmix | 22 Subunits | 1103 | 1092 | 99 |

According to one embodiment of the present invention, a typical rNP mean size diameter measurement is about 300 nm but may range from about 100 nm to about 400 nm with 300 nm a preferred diameter. The zeta potential may range from about −10 mv to about +10 mv. During the preparation procedures, charged particles are useful because the mutual charge repulsion keeps the suspension stable. The suspension zeta potential is reduced when haptoglobin is added. The mean diameter for this batch is within our target range. Polydispersity indices (PDI) for light scattering are an indication of the reliability of mean size measurement and the overall uniformity of the suspension. Values for PDI that are less than 0.2 are considered acceptable by the instrument manufacturer. The zeta potential is slightly negative, which reflects the availability of un-conjugated carboxyl group for subsequent haptoglobin attachment. During the preparation procedures, charged particles are useful because the mutual charge repulsion keeps the suspension stable. The suspension zeta potential is reduced when haptoglobin is added.

This approach is commonly used to control the degree of opsonization of particles in biofluids.

In another embodiment the rNPs were heldat room temperature for 3 weeks after which Hb was conjugated. The DLS of the sample was determined. The size of rNP was consistent and linking of Hp affected little to the size of rNP. The mean diameters and their standard deviations of rNP were subsequently measured over 12 weeks. These values were determined with DLS at room temperature. Both mean diameters and the standard deviations remained nearly constant.

The rNP was studied using optical microscopy (100× oil immersion lens) in PBS, plasma and blood. With the CCD camera, the total optical magnification is approximately 1,000×. Knowing that the size of RBC is 6-7 mm, the sizes of rNPs appear as small dark dots in photographs and are the order of a few hundred nanometers close to the limit of optical resolution of an optical microscope and correlate with the DLS values. These observations of nanoparticles seem to suggest that either rNP or rNP-Hpmix do not affect visually the plasma or RBC. The Rouleaux formation of RBC was mostly no more than usual observation of microscopic observation of the blood.

The core formulation did not react with ABO or Rh blood types. Hemolysis was tested by adding our core formulation after storage at room temperature and 37° C. with and without sterilization by autoclave. These emulsions and PBS (as negative control) were added at 20% by volume to normal human whole blood, and water at 10% by volume was used as a positive control. We have not experienced either reactivity or hemolysis. Tests with rNP-Hp were similar and no problem in animal studies were observed.

Figure 7:
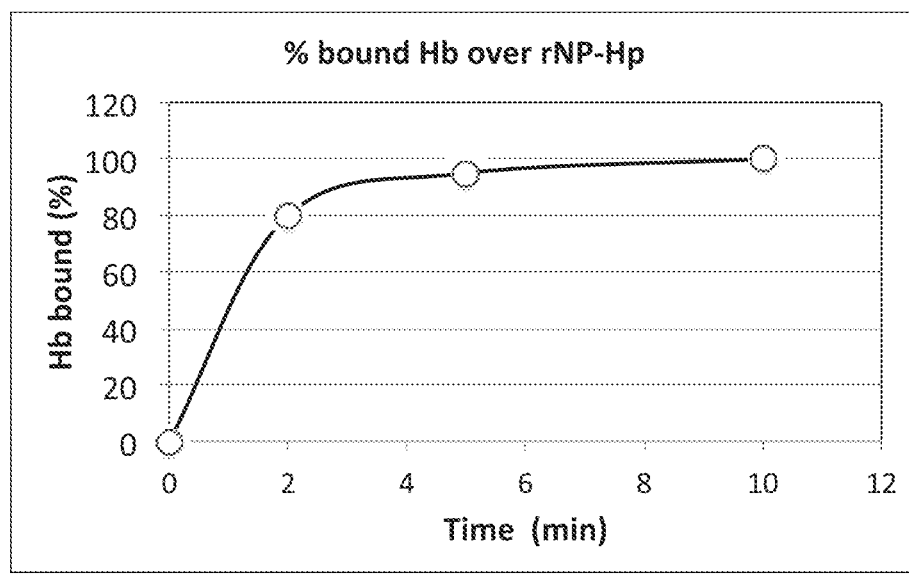
FIG. 7 is a graph of % bound Hb on the surface of rNP-Hp1-1 over time with gentle end-to-end mixing.

In PBS, the rate of reaction between Hb (molecules) and rNP-Hp (nanoparticle) with the mass ratio of HbA and Hp to be at 0.5, k rNP-Hp+Hb→rNP-HP-Hb, has been estimated with the end-to-end mixing device up to 10 minutes at the room temperature. After 2, 5 and 10 minutes of reactions the samples were collected and centrifuged to sediment rNP-Hp and rNP-HP-Hb to estimate the percentage of unreacted Hb remaining in solution spectrophotometrically and the results are shown in FIG. 7 as the % bound against the time of incubation. It is evident that after 2 minutes of mixing up to 80% of Hb were bound to rNP-Hp, but it took additional 8 minutes to compete the binding. Though the results demonstrated that entire Hb can be captured with this procedure, the procedure needs to be facilitated for it to perform in-line with the clinically accepted aphaeresis instrument.

To facilitate a reaction between rNP-Hp and HbS in blood during a time period of less than 400 sec such that a substantial portion of HpS is bound to rNP-Hp, there is a need to activate the nanoparticles beyond their thermal agitation and without mechanical stirring of the solution.

A device that facilitates the reaction between nanoparticles and molecules was investigated with a stable model system, namely, the reaction between ½ of 5,5'-dithiobis (succinimidyl-2-nitrobenzoate)(DSNB) and gold nanoparticles (AuNP). The reaction rates for crosslinking of DSNB with gold nanoparticles were compared between the end-to-end mixing and the laminar flow mixing. The crosslinking of DSNB with 100 nm AuNP was examined due to the presence of strong affinity of gold for sulfur. Cross linking in this reaction is easily detected with the decrease of Zeta potential of AuNP upon binding of DSNB. The rate of reaction under end-to-end mixing was tested for the reaction using the recipe described below:

1. Make 1 uM binding solution (diluted by borate buffer, pH 8.5).
2. Add 800 ul AuNP solution (In some exp, AuNP solution was mixed with glycerol.) into zeta potential cell/cuvette.
3. Measure the zeta potential of AuNP solution. (n=5)
4. Add 12 ul 1 uM binding solution into zeta potential cell/cuvette. Pipet the solution quickly (for mixing).
5. Measure the zeta potential of AuNPs and binding molecules.

Figure 8:
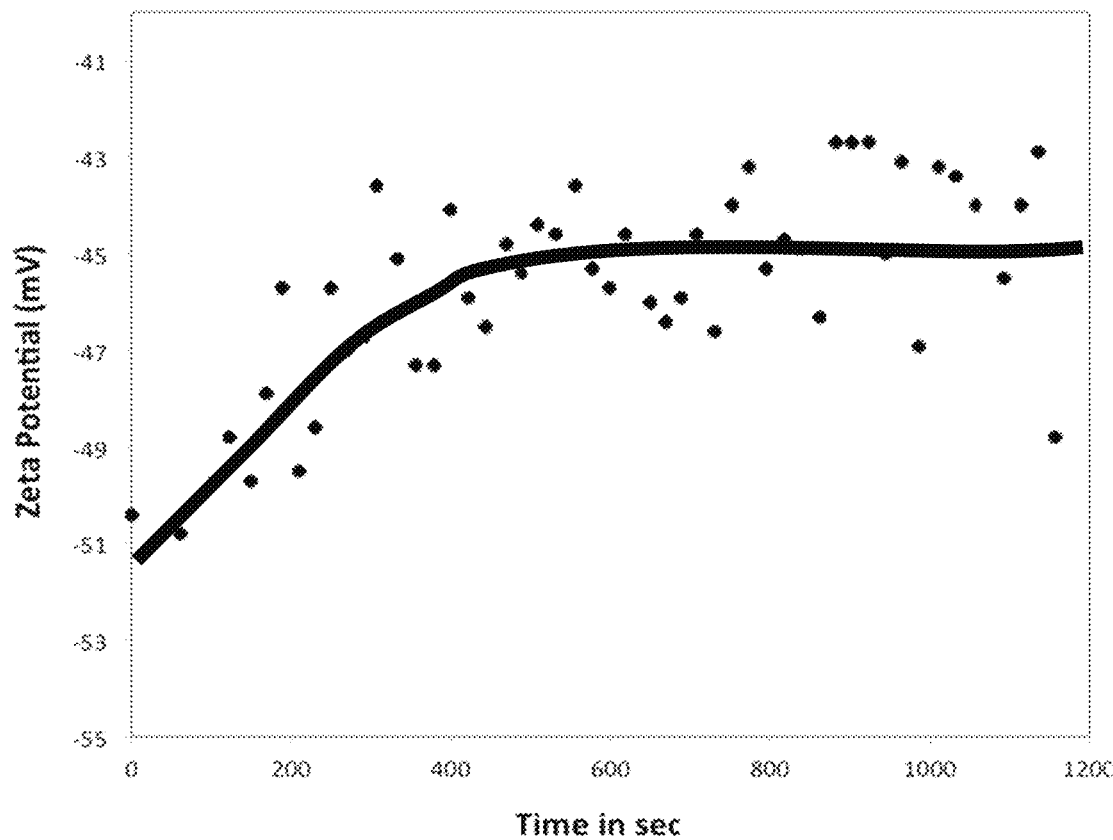
FIG. 8 is a graph showing time to bind DSNB over AuNP with side to side mixing.

Referring now to FIG. 8 the change of Zeta potential of AuNP in response to the attachment of DSNB on their surface during end-to-end mixing at room temperature. AuNP and DSNB were combined in solution using end-to-end mixing. The starting Zeta potential of AuNP was −50 mV. Reducing the zeta potential to −43 mV using a known aliquot of DSNB to displace the triply negatively charged citrate takes up to 600 seconds.

To determine if shorter reaction times would take place in laminar flow, one or more thin tubes of an embodiment of a laminar flow reaction device as described herein, was utilized with the same reaction conditions as described in FIG. 8.

Figure 9:
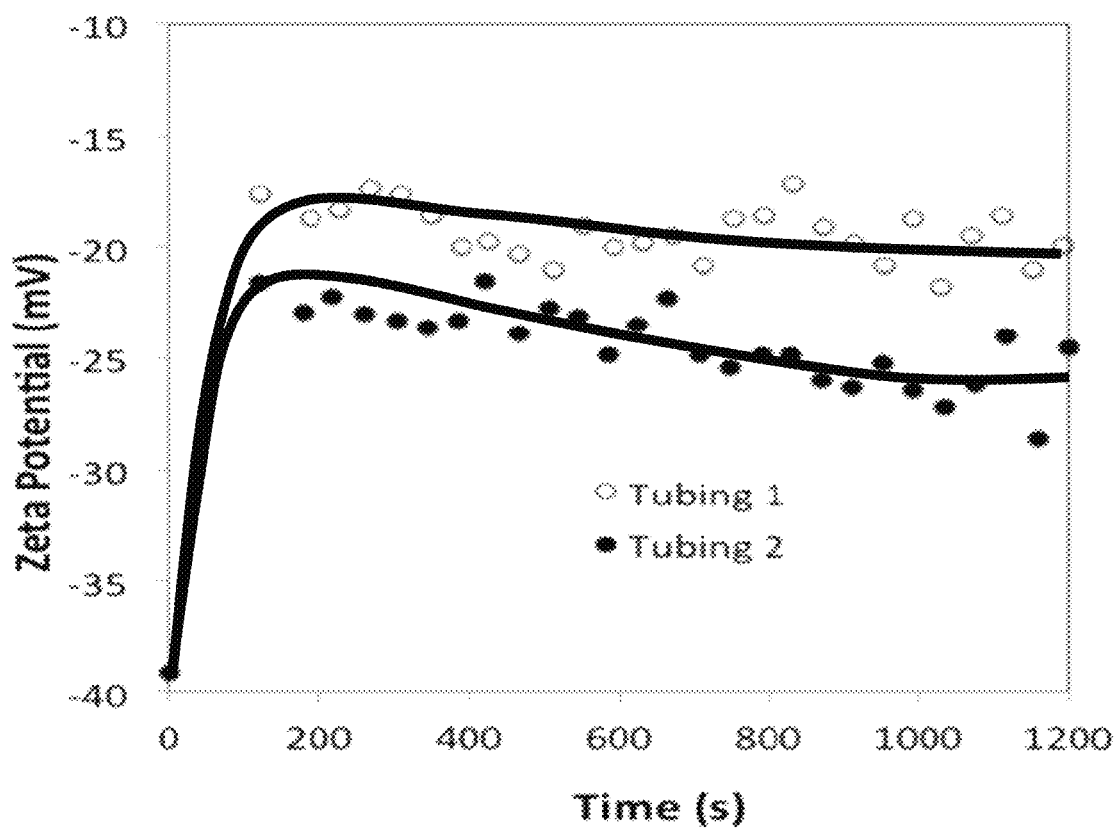
FIG. 9 illustrates time to bind DSNB on the AuNP using a LFRD mixing.

Referring now to FIG. 9, the Zeta potentials prior to entry into the device were −39 mV, but after two minutes of flow time, the potentials were moved to −18 and −22 mV for Tubing 1 (thicker tubes 3 mm diameter) and Tubing 2 (thinner tubes 1.5 mm diameter), respectfully. During the continued flow of solutions, small changes in the potentials were observed. During the initial two minutes significant neutralization of surface charges took place, possibly due to cross linking of DSNB on the surface of AuNP. Such dramatic quick changes in the Zeta potentials were not observed upon mechanical mixing of these two reactants as shown in either FIG. 8. The change of Zeta potential of AuNP in response to the attachment of DSNB at different distances in the LFRD (i.e. different residence times). AuNP and DSNB were combined in LFRD. Two LFRD units using tubing of two different diameters (Tubing 1 is larger diameter than Tubing 2) were compared. The fluid flow rate was 1 ml/min in each tube. The starting Zeta potential of AuNP was −40 mV. At a point in the LFRD corresponding to 100 sec residence time a large change in zeta potential was observed. More efficient reaction was seen in the larger diameter tubing. At points in the LFRD corresponding to residence times greater than about 500 s, the net % of reaction was less than at the beginning of the tubing. This was much less in larger diameter tubing. This may be related to higher rates of damage to the materials in the smaller diameter tubes. The observations were based on the Zeta potential prior to mixing and the change in Zeta potential as a result of reaction within the tubes after two minutes at the exits of the tubes.

The results of b demonstrate that within 100 seconds, or six times faster than the simple mechanical mixing of solution observed in FIG. 8, the reactions are completed. The reaction could have been completed faster than 100 sec, but that was the limitation of the detection time of this procedure.

Laminar flow in a straight tube provides for mixing of the rNP-Hp particles in solution. The mixing chamber preferably comprises a substantially straight tube. The tube can be oriented in a vertical orientation or in a horizontal orientation. A substantially straight tube be may include a small degree of curvature along the axis of the tube along its length so long as the curvature does not prevent laminar flow within the tube. In one embodiment of the present invention, unlike previous descriptions of mixing chambers, no spiral element occurs in the mixing chamber and no turbulence is mechanically introduced within the tubes of the laminar flow mixing device.

Figure 4:
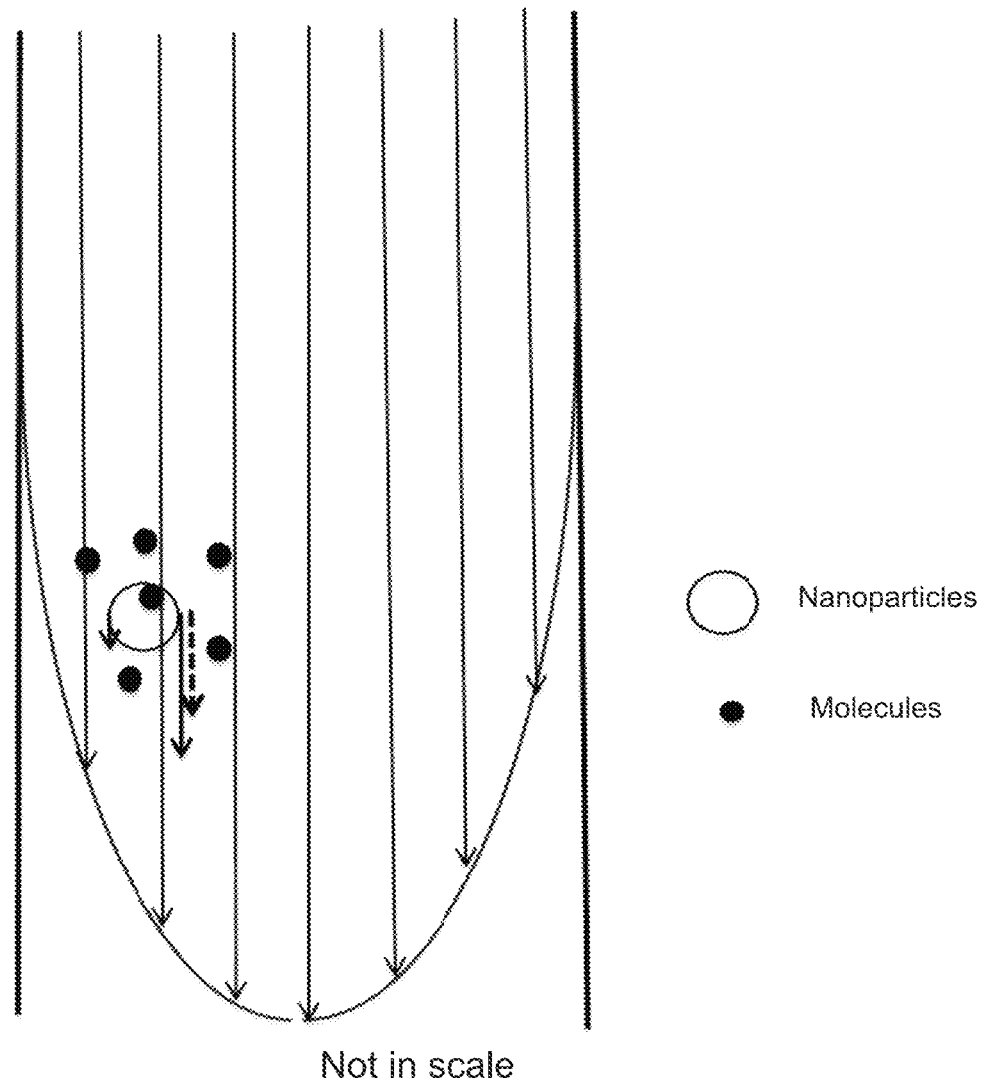
FIG. 4 is an illustration of nanoparticles and molecules in a fluid moving in a tube having a laminar flow.

Referring now to FIG. 4, a laminar flow mixing device is illustrated according to one embodiment wherein fluid flows in a tube of sufficient length and diameter to obtain a laminar flow to permit mixing. To explain the unexpected results of the experimental data obtained with the laminar flow mixing device, it is hypothesized that the rate of chemical reaction between nanoparticles (open circle) capable of binding a number of molecules (dirk circles) passing through a thin tube is affected by the laminar flow created in the tube. The rates of laminar flows are shown in thin long arrows along with the overall flow of the liquid. Although the drawing is not to scale, the drawing illustrates that the nanoparticle is large enough to respond to the difference in the laminar flow rates on opposite sides of the surface of the nanoparticle as shown in the black arrows and the difference of the two vectors appears as the red arrow. Each line represents a different rate of flow. With the fastest rate in the center and slowest rate at the edge, a parabolic flow rate is established thereby introducing shear with the magnitude of the force on either side of the NP being different. Referring now to FIG. 4. facilitation of chemical reactions between nanoparticles and molecules in the laminar flow liquid without increasing temperature is illustrated according to one embodiment of the present invention. It is hypothesized that the rate of chemical reaction between nanoparticles (open circle) capable of binding a number of molecules (dirk circles) passing through a thin tube is affected by the laminar flow created in the tube. The rates of laminar flows are shown in thin long arrows along with the overall flow of the liquid. Although the drawing is not in scale, the nanoparticle is large enough to respond to the difference in the laminar flow rate on both sides of the surface as shown in the black arrows and the difference of the two appears as the red arrow. As a consequence, it is hypothesized that the nanoparticle spins while it continues to move down along with the bulk flow rate. The spin is equivalent to stirring of the nanoparticles in the flow and exposes more of its active site reacting to the molecules moving under thermal agitation while moving along the bulk flow of the liquid. The consequence will be the facilitated enhanced reactions between the two reactants, even without increasing the temperature. The degree of facilitation depends upon the size of nanoparticles, the liquid flow rate, viscosity of the liquid and diameter of the tube.

Figure 10:
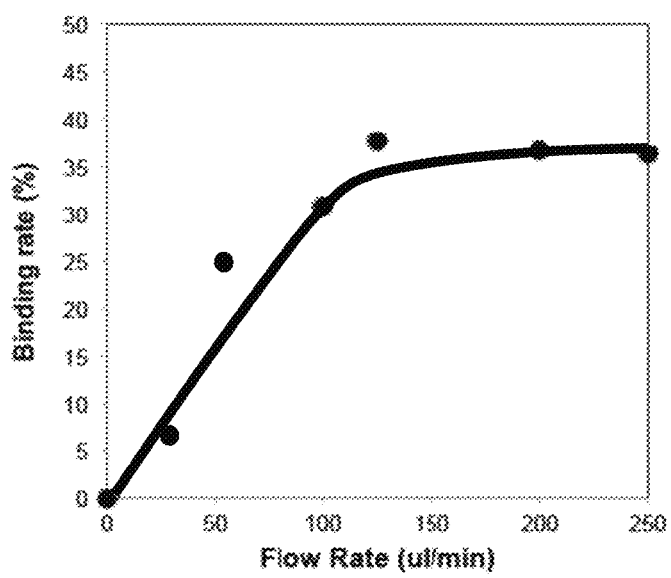
FIG. 10 is a graph of % of HB bound to rNP-Hp in plasma after flow at different rates through a laminar flow mixing device ("LFRD") with 2 minute residence time.

FIG. 10 demonstrates that the enhanced mixing with a laminar flow reaction device according to an embodiment of the present invention facilitates a similar enhanced reaction between rNP-Hp and Hb. The Hb (2.62 µM) and rNP-Hp (Hp 0.25 µM) were suspended in PBS. Using 0.86 mm diameter of tube they were mixed for 2 minutes and at different flow rates using peristaltic pumps as described previously. The products were quickly centrifuged to spin out rNP-Hp-Hb and the remaining concentration of unreacted Hb in solution was spectrophotometrically determined.

Figure 11:
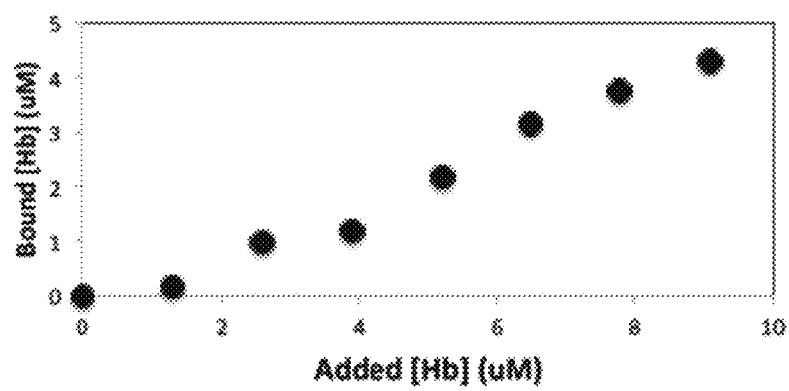
FIG. 11 is a graph showing the concentration of rNP-Hp bound Hb versus amount of added HB determined over a physiologically relevant range.
Figure 12:
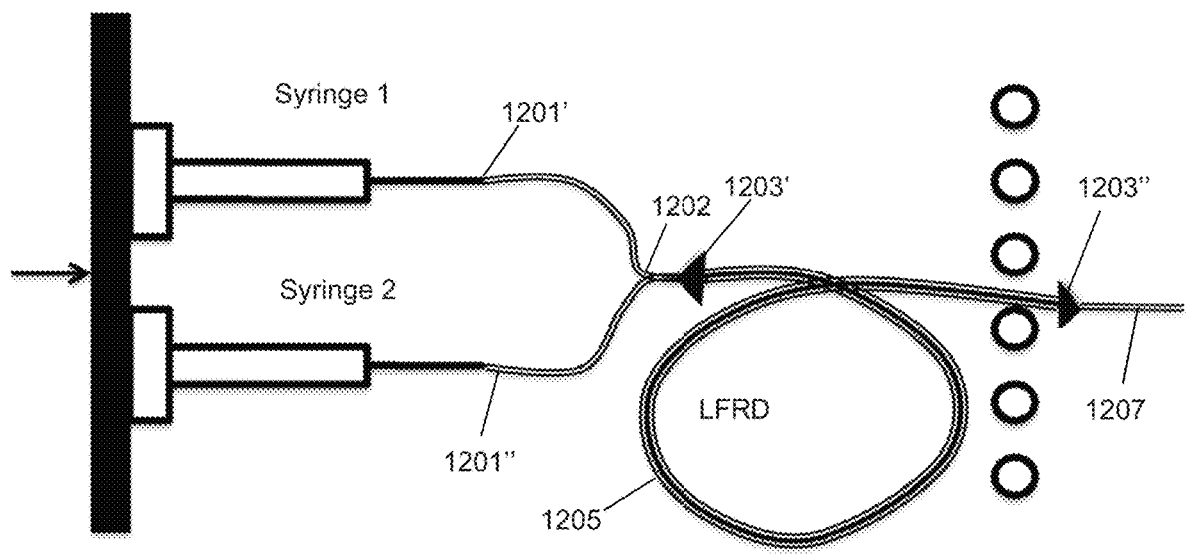
FIG. 12 is an alternative form of an LFRD device with a "Y" tube and simultaneously driven syringes.

Referring now to FIG. 11, if there is excess quantity of Hb, the remaining unreacted Hb concentration, which is spectrophotometrically determined, will not reach zero. In this particular experiment, about 35% of Hb remained in solution unreacted. It is important to note that within 2 minutes the reaction is completed when mixed at the flow rate of 100 mL/min. The mixing ratio of the reactants may not be optimal, but within two minutes the reaction is completed as evidenced by the fact that the binding percentage has reached the plateau. Within the range of about 1.0-3.5 mm diameter of tubing, FIG. 11 illustrates that the rate of reaction of this type appears to be the same. It has been shown that after 2 minutes of gentle tipping mixing the reaction between rNP-Hp with Hb was completed only 40%, but under laminar flow at the rate of 32-33 ml/min for 2 min, nearly 100% of Hb were bound to rNP-Hp. Unexpectedly without mechanical mixing an increase reaction rate was observed in laminar flow.

Further the capacity of a LFRD device is demonstrated. An example of linear dependence of bound Hb over the added Hb suggesting the capacity of LFRD is not exceeded within this range of concentration of Hb.

During the tests, it is important to be aware that the operation is being carried out within the concentration limit of LFRD. How much HbA can be bound with rNP-Hp in the LFRD depends on the type of LFRD. Such capacity depends on the number of reaction tubes and their diameter and length, as well as the rate of liquid flow through the tubes.

It was observed that mixing the rNP-Hp with the blood in a tube using laminar flow caused an increase in the percent of Hp bound to rNP-Hp. Therefore the reactions between rNP-Hp and Hb are facilitated to keep pace with the blood flow rate through the aphaeresis instrument.

Another embodiment of the present invention provides a laminar flow-facilitated reaction device (LFRD), where rNP-Hp will rapidly bind with PFH at high efficiency exo-corporeally. The LFRD enhances the reaction of the rNP-Hp with HbS such that the blood returning to the patient after aphaeresis is depleted of about 99% of the HbS in the blood. In an alternative embodiment the blood returning to the patient is depleted of between about 90-100% HbS, 80-90% HbS, 70-80% HbS or 50-70% HbS.

In one embodiment, the rNP-Hp-Hb formed after passing through the LFRD will be collected within the aphaeresis instrument to be discarded or analyzed, while "cleaned" blood returns to the patient. The efficiency of the device operation will be monitored by measuring the PFH levels in the fluid entering the mixing chamber and exiting the aphaeresis unit.

The LFRD is designed to minimize blood lysis or not to increase blood cell lysis above the base level that occurs during aphaeresis or alternatively not to cause significant blood cell lysis. The amount of rNP-Hp used in this procedure should not only remove the already existing PFH in the patient's blood stream, but may also be able to mitigate hemoglobin released from the aphaeresis process. It is known that during aphaeresis blood gets lysed. The aphaeresis system as described herein can use to remove the hemoglobin released during treatment in additional to hemoglobin lysed during disease.

At slow flow rates inside the thin tubes, nanoparticles (i.e. rNP-Hp) will experience increased collision frequencies with small molecules (i.e. free Hb), and this would increase the observed rate of binding reaction. The reasoning for this has to do with the nature of fluid velocity profile in each tube having laminar flow as shown in FIG. 4. The differing ability of the rNP-Hp and Hb to move axially across the tube, and whether the size of the rNP-Hp is such that one part of the nanoparticle samples a different fluid velocity profile as compared to the opposing side of the same nanoparticle or of another nanoparticle flowing at a different velocity. Depending on the balance of these conditions nanoparticles may spin while flowing through the tube creating micro-currents that accelerate the collisions with smaller soluble molecules such as free Hb. This motion also allows the reactive surface of the particles (unbound Hp on the surface of the nanoparticle) to be available to bind free Hb, since an area already occupied by Hb will not have a fixed orientation relative to the fluid flow. Total flow rate: F2=n*f2 with n being the number of tubes. The flow rate in each tube is f2. The cross sectional area of each tube is a2. The total cross sectional area is: A2=n*a2. Rate of flow volume is: W2=F2*A2=(n*f2)*(n*a2)=n2*(f2*a2). Since W1=W2, then F1*A1=F2*A2=(n*f2)*(n*a2)

Figure 5:
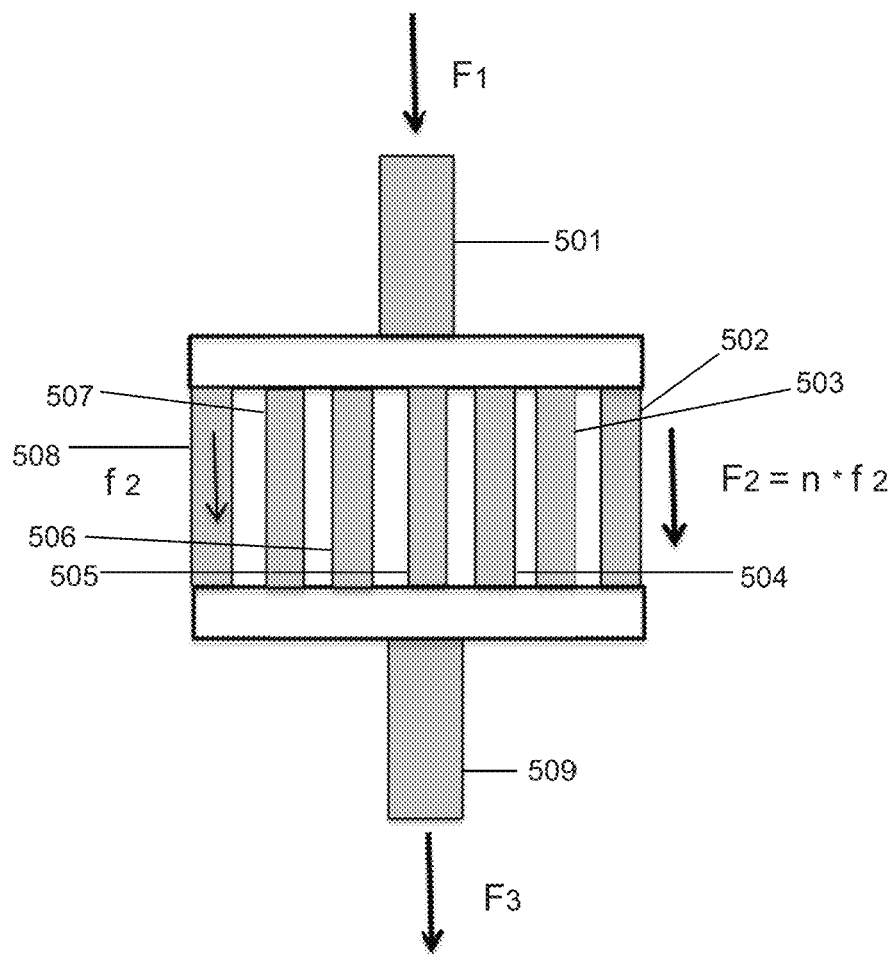
FIG. 5 is an illustration of a laminar flow reaction device according to one embodiment of the present invention.
Figure 6:
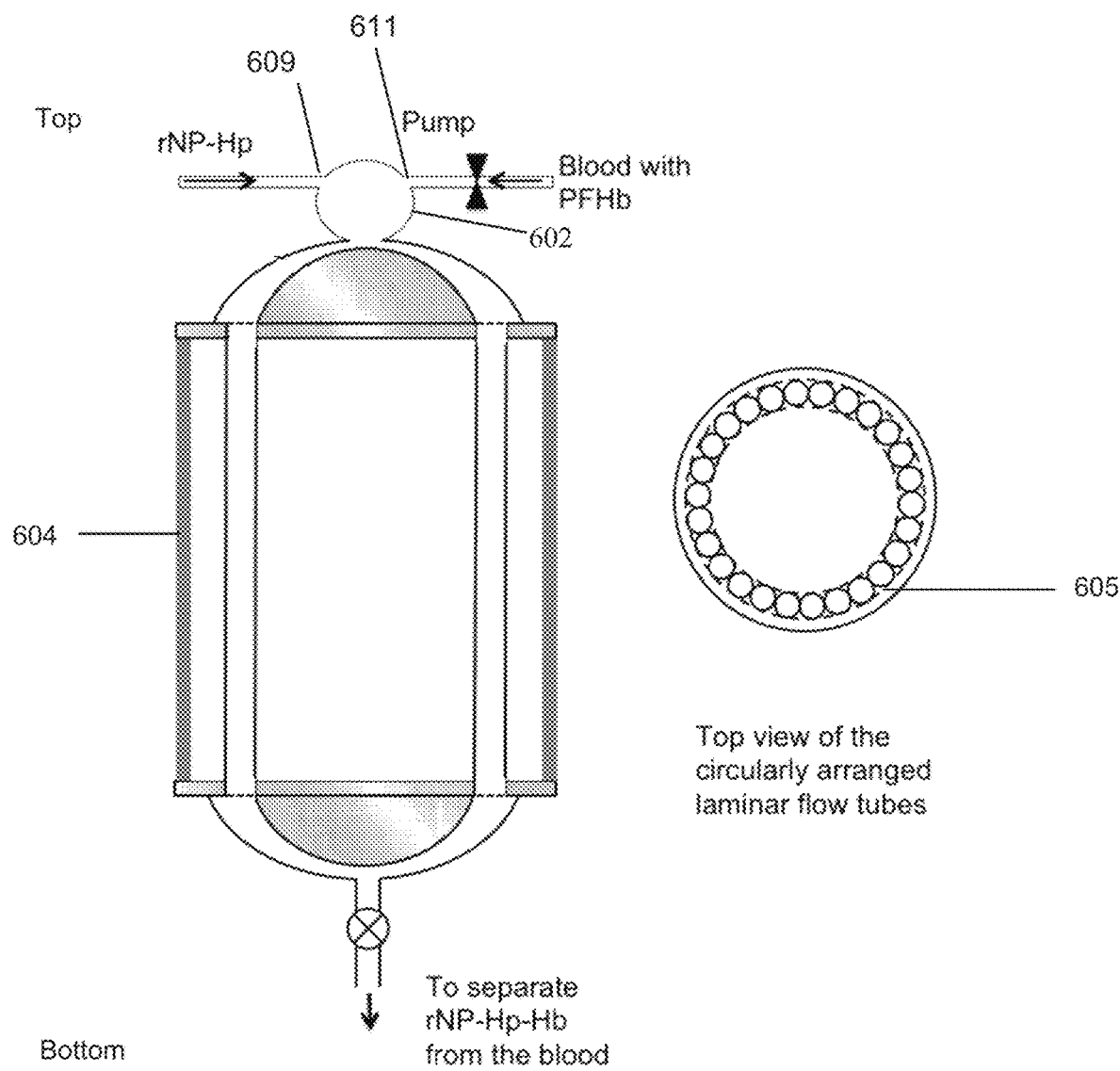
FIG. 6 is a diagram of a laminar flow reaction device according to one embodiment of the present invention.

F1/f2=n2*a2/A1. Since n>1, by having more than one thinner tubes, a2<A1,

Then, f2<F1. In other words, the flow rate in the thin tubes could be made slower than that of the incoming larger tube. If the length of the thin tube is l2, the residence time t2 will be, t2=l2/f2. Thus, the residence time is dependent on both parameters. It will increase in proportion to the length of the thin tube and to the decrease of the flow rate in the thin tube. In other words, this device will extend the time for reaction under controlled Lamella flow for facilitated reaction of HbS and Hp bound to nanoparticles. Referring now to FIG. 5, an embodiment of the mixing chamber is provided. In the tubing as described in FIG. 4, the particles and blood preferably undergo laminar flow while being mixed for a desired duration of time as the blood and reactants pass through the length of the tube. The mixing efficiency may thus be varied widely by controlling the rate of blood flow, the configuration of tubing (including its diameter), and the number of tubes used. A laminar mixing flow device is illustrated where the entering liquid flow rate is $F_1$ in tube 501 and the cross sectional area of tube 501 entering the tube is $A_1$. The rate of flow volume is $W_1=F_1*A_1$. Subsequently, the fluid entering the tube is divided into n=7 tubes 501-508 of smaller cross sectional areas of $a_2$ with each having a flow rate of $f_2$. The flow rate $F_2$ in this region is $f_2*n$. The total cross sectional area of this region, $n \times a_2$ could be made=about $A_1$. Then the liquid flow rate in each tube f2 will be less than F1. In other words, the liquid flow rate in the thin tubes is f2<F1. The fluid exiting tubes 501-508 is recombined into tube 509 which has a flow rate of F3 which is about equal to F1. The tubes 501-508 are arranged in parallel and/or stacked but can also be arranged adjacent to each other in a circular fashion as is illustrated in FIG. 6.

Figure 13A:
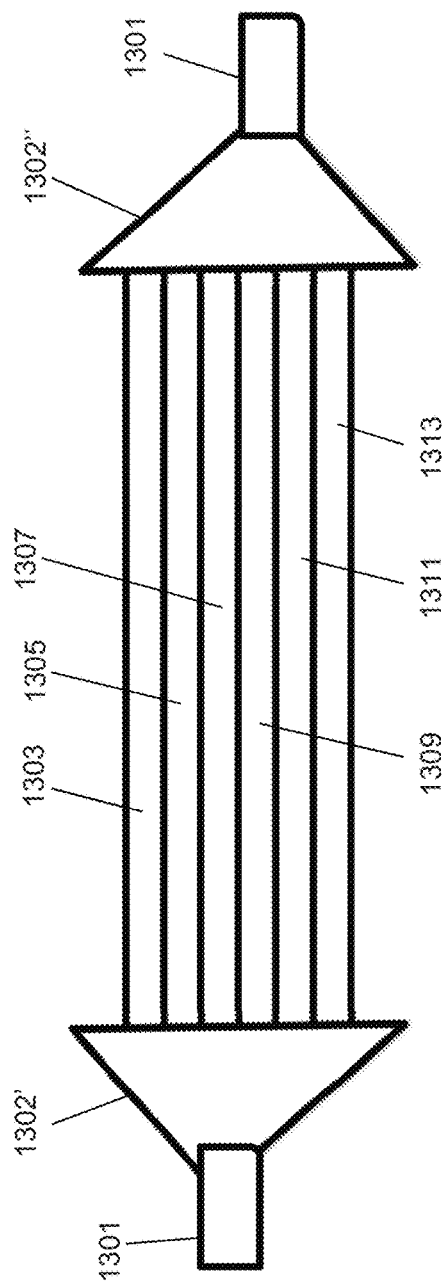
FIG. 13A-B is an illustration of a multiple tube LFRD configuration.
Figure 13B:
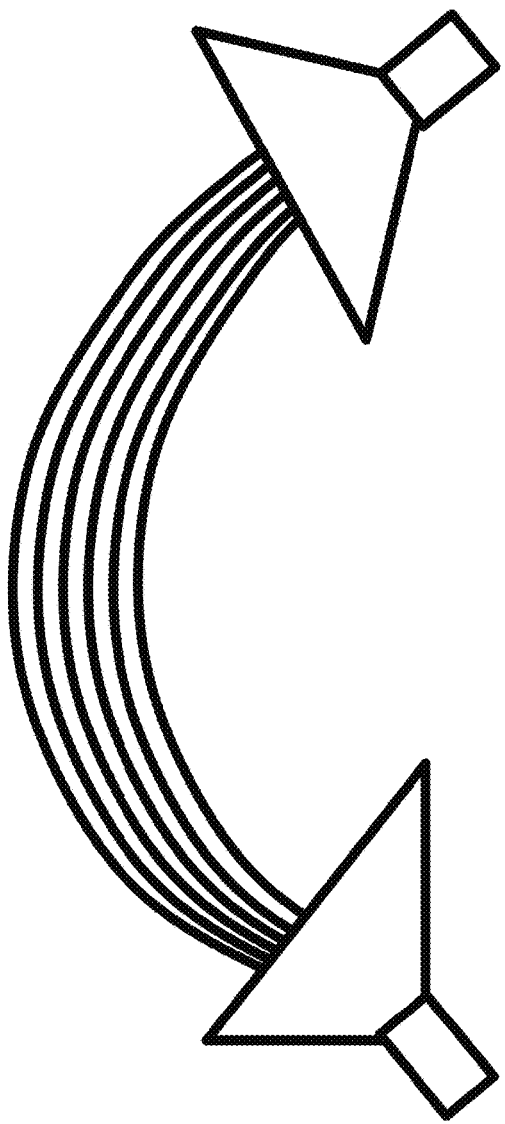

To demonstrate the effect of enhanced mixing with laminar flow, two solutions each containing a reactant were supplied to a tube 1201' and 1201" either with a pair of peristaltic pumps or syringes with the solutions to be mixed either with a "T" or "Y" 1202 shaped tube. The mixed solutions were introduced into a plurality of thin tubes 1205 of a defined length to form laminar flow to carry the two reactants along the length of the thin tubes in the laminar flow. The solutions entered the plurality of the thin tubes after passing through a funnel 1203' to help separate the mixed solutions into the plurality of thin tubes. The plurality of thin tubes connect with a single tube 1207 via funnel 1203" so that all of the volume flowing in the plurality of thin tubes is carried toward the aphaeresis rotor via tube 1207. Additionally, the two reactants are a target in solution pushed by syringe 1 in tube 1201' and a capture molecule pushed by syringe 2 in tube 1201". The capture molecule binds specifically to the target. Additional embodiments used in this study are illustrated in FIG. 13 wherein the thin tubes 1303, 1305, 1307, 1309, 1311, 1313 are shown with a first tube 1301 connected to the plurality of tubes via a funnel 1302' and a second funnel 1302" connects the plurality of tubes to a second tube 1301 at the opposite end. Tube 1301 has a larger ID than thin tubes 1303, 1305, 1307, 1309, 1311, 1313. The thin tubes 1303, 1305, 1307, 1309, 1311, 1313 are shown with a slight curve along the length of the tube in the lower image which does not prevent laminar flow of fluids in the thin tubes 1303, 1305, 1307, 1309, 1311, 1313. When the capture molecule was Hp on the surface of rNP and the target was Hb and the laminar flow mixing device was operated optimally, it was confirmed that no rNP-Hp exited the rotor once equilibrium in the rotor was established and a continuous feed of rNP-Hp was delivered to the aphaeresis loop at a rate less than that of the rate of flowing blood (i.e. less than 30 ml/min). An extreme situation in which rNP-Hp was injected at a rate faster than blood flow (>30 ml/min) was also tested to determine what would be the worst case scenario for leakage of rNP into the high density port. In this case we found no particles exiting the centrifuge rotor either, despite the high concentration of particles detected at point 3 of FIG. 15, after the laminar flow reaction device (LFRD) but before the rotor.

Figure 15:
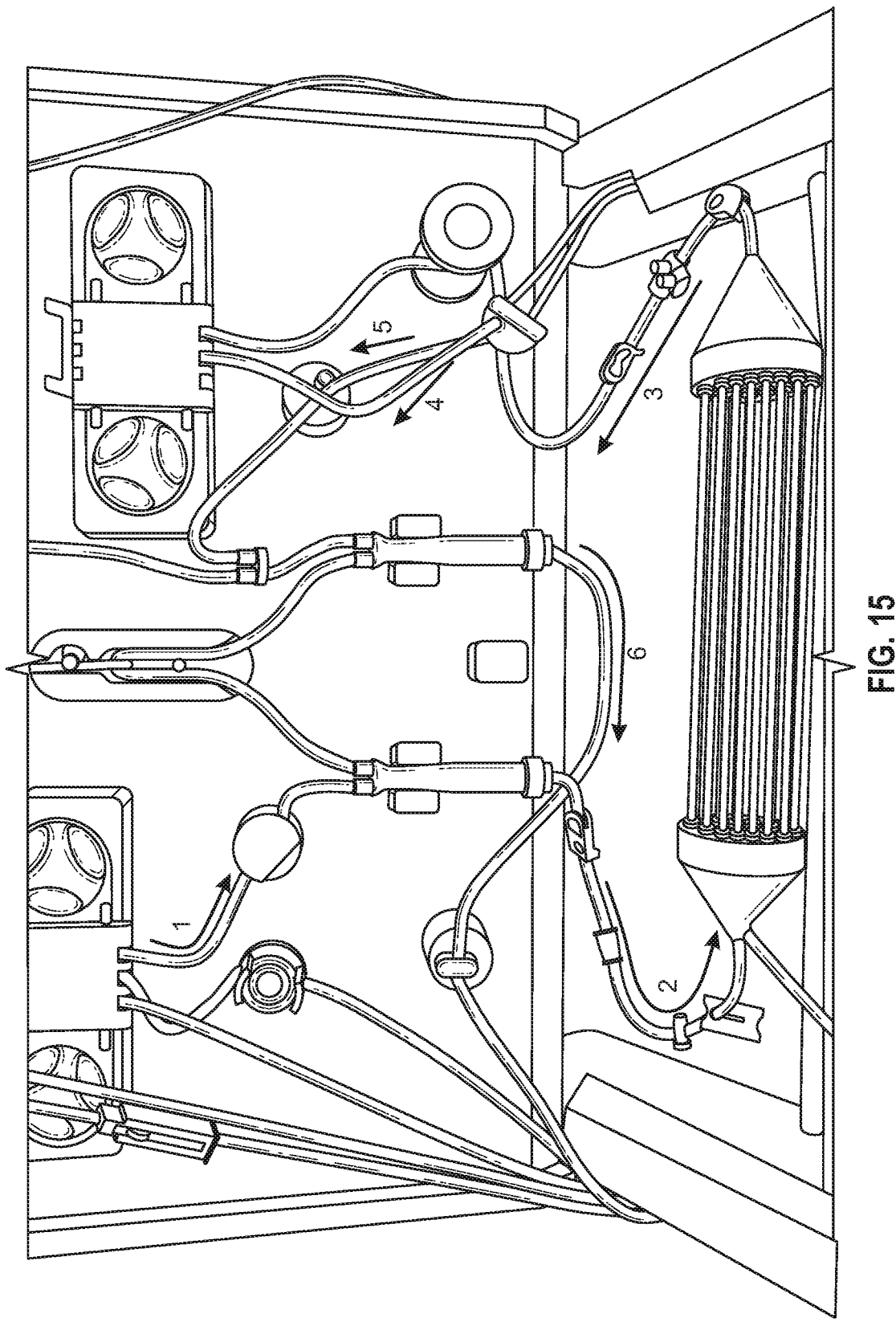
FIG. 15 illustrates a multitube LFRD according to one embodiment of the present invention.

Referring now to FIG. 14 animal 1-4 represent control animals and test of a LFRD as a component of the aphaeresis loop. A fifth animal was tested to demonstrate efficacy and safety of rNP-Hp. Panels A-B represent moderate Hb concentration in blood entering the LFRD and complete removal of this extra free Hb post aphaeresis removal of rNP-Hp-Hp. Panels C-D show efficient removal of a much higher amount of Hb. The concentration span of Hb in these experiments is 3.3 uM to 8.9 uM. Results of Hb capture in domestic swine (~50 kg) using a laminar flow reaction device combined with aphaeresis is provided. Four measurements of Hb content in circulating blood, before the LFRD (solid black line), with added Hb (dashed) and after the LFRD and aphaeretic removal of rNP-Hp-Hb (dotted line). The LFRD/aphaeresis process returns the level of free Hb in plasma to original levels, despite an intentional spike in Hb concentration. In this experiment, a Cobe Spectra Aphaeresis system was combined with a laminar flow reaction device having 32 tubes of about 30 cm length and an inner diameter of about 3 mm. Blood enters the system at position 1-2 and enters the laminar flow reaction device positioned between point 2 and 3. The blood flows at about 1 ml per minute and has about a 2 min residence time in the laminar flow reaction device. The blood is carried in the tubing of the aphaeresis loop to the low density port 4 and the high density port 5-6. Not seen in FIG. 15 is the centrifuge rotor where the blood is separated into components based upon density. Without the laminar flow reaction device the rNP-Hp added to the blood would not have the time to bind free Hb and the blood returning to the animal would contain free Hb above that of control.

Referring now to FIG. 15, a Cobe Spectra aphaeresis instrument was combined with a LFRD according to one embodiment of the present invention. A fluid flow can be generated by gas or electronic pressure induced syringe pump, peristaltic pump, other mechanical pump, or anatomical pump such as the heart. The syringe pump option shown in the drawing offers precise mixing for testing, but only discontinuous flow use. While the Cobe Spectra aphaeresis device was used here, the LFRD and the method of use can be combined with any aphaeresis system.

In one embodiment of the present invention exo-corporeal removal of plasma free hemoglobin (PFH) from the blood with the exo-corporeal introduction of rNP-Hp to the blood that is transiently directed outside of the body of the patient and occurs before the blood is returned to the patient. It was observed that mixing the rNP-Hp with the blood in a tube using laminar flow caused an increase in the percent of Hp bound to rNP-Hp. Therefore the reactions between rNP-Hp and Hb are facilitated to keep pace with the blood flow rate through an aphaeresis instrument.

Another embodiment of the present invention provides a laminar flow-facilitated reaction device (LFRD), where rNP-Hp will rapidly bind with PFH at high efficiency exo-corporeally. The LFRD enhances the reaction of the rNP-Hp with HbS such that the blood returning to the patient after aphaeresis is depleted of about 99% of the HbS in the blood. In an alternative embodiment the blood returning to the patient is depleted of between about 90-100% HbS, 80-90% HbS, 70-80% HbS or 50-70% HbS.

In one embodiment, the rNP-Hp-Hb formed after passing through the laminar flow reaction device will be collected within the aphaeresis instrument to be discarded or analyzed, while "cleaned" blood returns to the patient. The efficiency of the device operation will be monitored by measuring the PFH levels in the fluid entering the mixing chamber and exiting the aphaeresis unit.

The LFRD is designed to minimize blood lysis or not to increase blood cell lysis above the base level that occurs during aphaeresis or alternatively not to cause significant blood cell lysis. The amount of rNP-Hp used in this procedure should not only remove the already existing PFH in the patient's blood stream, but may also be able to mitigate hemoglobin released from the aphaeresis process.

One embodiment of the present invention is a mixing device as illustrated in FIG. 6. The blood with plasma free hemoglobin (PFH) and rNP-Hp, that captures Hb, enters into a small mixing chamber having a circular cross section 602 via a first inlet 611 and a second inlet 609 respectively at the controlled flow rate introduced with a peristaltic pump and/or a syringe pump, for example. The mixed solution in the mixing chamber 602, flows to the circularly positioned plurality of thin tubes (left side of the FIG. 6). Each thin tube 605 will be of desired diameter and length. Each of the circularly positioned tubes 605 should receive equal concentrations of the blood, PFH and rNP-Hp, and the mixture transits through the thin tube via laminar flow. The tubes are enclosed in a support 604 to maintain the thin tubes in a desired orientation. The effluent will be collected at the bottom end of the support. The volume of blood from the individual thin tubes is recombined into a single exit tube connected to the bottom end of the support. The blood thereafter transits through the exit tube and enters into the aphaeresis instrument to collect Hb bound to rNP-Hp. Usually, the blood will enter a clinically used aphaeresis instrument at the rate of 32 ml/min. (for a 150 lb patient) while the centrifuge rotor spins at the rate of about 3,000 rpm. The blood components are separated according to their densities ranging from the lowest density of plasma (1.025-1.029) to the highest density of aged RBC (1.110) and usually separated into three major components. With minor operational adjustments, the same aphaeresis instrument can be used for separation of blood components and rNP, of which density varies between 1.5-1.9. A typical aphaeresis instrument or aphaeresis blood separation system as used herein includes a centrifuge rotor (or filler), a separation tubing inserted into the centrifuge rotor for rotating therewith wherein blood is separated into red blood cells, white blood cells, platelets, plasma and other components based upon the density of each in the separation tubing during rotation of the centrifuge rotor. Each density separated component is collected outside of the centrifuge rotor through each specific tube continuously. Operation of aphaeresis can be performed under sterile condition with sterile tubing directing blood from the patient to the aphaeresis instrument and thereafter directing the blood from the aphaeresis instrument back to the patient.

One embodiment of the laminar flow mixing device can accommodate a flow rate of between 32-33 ml/min+/−50% so long as the flow rate does not result in hemolysis of the blood. An aphaeresis instrument can accommodate higher flow rates but the limiting step is reentry into the patient. During aphaeresis according to one embodiment of the present invention the max amount of blood outside of the body is about 300 ml from a 150 lb man which has about 5 liters of blood total. Therefore the amount of blood outside of the body represents less than 10% of the total blood volume of the patient.

In one embodiment of the present invention the tubes are to be arranged vertically vs horizontally as positioning the tubes horizontally may bias the distribution of the rNP components.

The preceding examples can be repeated with similar success by substituting the generically or specifically described reactants and/or operating conditions of this invention for other nanoparticles and molecules. The following Tables 7-9 provide additional examples of conditions that will promote enhanced mixing of nanoparticles and molecules as compared to mixing the same concentration of nanoparticles and molecules in a closed container with mechanical mixing (e.g. end-to end mixing).

TABLE 7

BLOOD APHAERESIS IN PLASMA

| parameter | range | preferred |
| --- | --- | --- |
| Flow rate in a single tube | 0.5-3 ml/min | 1 ml/min |
| Total flow rate | 20 to 40 ml/min | 32 ml/min |
| Tubing diameter | 1-5 mm | 3 mm |
| Number of tubes | 1-64 | 32 |
| Residence time of fluid in the whole unit | 0.5-5 minutes | 2 |
| Fluid pressure | 100-200 mmHg | 120 mmHg |
| Ratio of nanoparticle diameter to molecule | 10-110 | 60 |
| Shape of nanoparticle | sphere, oval, platelet, rod | sphere |
| Reynolds number | 1 to 10 | 3 |
| density of nanoparticle | 1.3 to 2.5 | 1.9 |
| % reaction completed | 50-100% | 70% |
| Tubing length (m) | .001-24 | 0.5 |

TABLE 8

Nanoparticle reactions in water

| parameter | range | preferred |
| --- | --- | --- |
| Flow rate in a single tube | 0.5-10 ml/min | 5 ml/min |
| Total flow rate | 20 to 500 ml/min | 100 ml/min |
| Tubing diameter | 1-5 mm | 3 mm |
| Number of tubes | 5-500 | 50 |
| Residence time of fluid in the unit | 0.5-10 minutes | 2 |
| Fluid pressure | 100-50000 mmHg | 500 mmHg |
| Ratio of nanoparticle diameter to molecule | 10-100 | 60 |
| Shape of nanoparticle | sphere, oval, platelet, rod | sphere |
| Reynolds number | 1 to 500 | 50 |
| density of nanoparticle | 1.05 to 2.2 | 1.3 |
| % reaction completed | 70-100% | 100% |
| Tubing length (m) | .001-240 | 0.5 |

TABLE 9

NANOPARTICLE REACTIONS IN HIGH DENSITY FLUID

| parameter | range | preferred |
|---|---|---|
| Flow rate in a single tube | 0.5-10 ml/min | 5 ml/min |
| Total flow rate | 20 to 500 ml/min | 100 ml/min |
| Tubing diameter | 1-5 mm | 3 mm |
| Number of tubes | 5-500 | 50 |
| Residence time of fluid in the unit | 0.5-10 minutes | 2 |
| Fluid pressure | 100-50000 mmHg | 500 mmHg |
| Ratio of nanoparticle diameter to molecule | 10-110 | 60 |
| Shape of nanoparticle | sphere, oval, platelet, rod | sphere |
| Reynolds number | 1 to 500 | 100 |
| density of nanoparticle | 1.2 to 5 | 2.5 |
| % reaction completed | 70-100% | 100% |
| Tubing length (m) | .001-240 | 0.5 |

In addition to the nanoparticles discussed, the following nanoparticles may also provide therapeutic benefit to a patient.

Iron Chelation Using Desferoxamine-Conjugated High Density Particles

Iron chelation using high density nanoparticles was studied by conjugating the iron chelator Desferoxamine (DFO) onto NHS-activated magnetic beads (MB, 2 g/ml, 1 μm diameter). The DFO and MB were reacted in 50 mM sodium borate buffer (pH 8), and the binding capacity of DFO to MB is estimated to be about 14.74 μg/mg MB. Since free iron is considered to be toxic at >60 μM, the DFO conjugated MB solution were mixed with 60 μM $Fe^{3+}$ ($Fe(NO_3)_3$ $9H_2O$) in PBS for 1 hour. The results show the DFO-MB complex can chelate iron, but not as well as DFO only. The chelating efficiency of DFO-MB complex was about 58% compared to 99% for free DFO. The data also shows approximately 13% non-specific iron binding on DFO-free MB. Correcting for the non-specific binding results in a DFO-MB iron chelating efficiency of approximately 45%.

Oxygen Carrying Capacity of High-Density Particles

Retrievable high-density submicron particles (rNP) were formulated using 3.1 mmol 1,2-dioleoyl-sn-glycero-3-phosphocholine (DOPC), 163 μmol 1,2-dioleoyl-sn-glycero-3-phosphoethanolamine-N-[methoxy(polyethylene glycol)-1000], 20% Vol perfluoroctanylbromide (PFOB) and 80% Vol PBS. The lipids (in chloroform) were mixed, rotovaped to dryness and vacuum dessicated for 3 days. They were reconstituted in 120 ml PBS. PFOB (30 ml) was added and the mixture emulsified (5000 rpm) for 1 minute to form uniform emulsion. The emulsion was homogenized at 30K× psi×10 passes to form 230 nm particles. The formulation was split and half stored at room temperature (21° C.) and half stored at 37° C. These particles were used as oxygen carriers. A stop-flow apparatus was used to determine the oxygen capacity of the particles, although any method detecting the spectral change of deoxygenated hemoglobin upon mixing could have been used. At 20% Vol PFOB is expected to carry ~19.9 Mol % $O_2$. The $O_2$ capacity of the formulation stored at room temperature and 37° C. was 16.7 Mol % and 14.8 Mol %, respectively. These particles are also expected to be $CO_2$ scavengers.

Note that in the specification and claims, "about" or "approximately" means within twenty percent (20%) of the numerical amount cited.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An aphaeresis apparatus for removing high density nanoparticles functionalized with a capture molecule from a biological fluid that is flowing within the aphaeresis apparatus, the apparatus comprising:
    a mixing chamber having a circular cross section upstream of a plurality (n) of tubes with each tube of the plurality of tubes having an inner diameter of a2 which is between about 1-5 mm and a length of l2 which is between about 0.001-24 m through which each tube of the plurality of tubes permits stable laminar flow of the biological fluid at a flow rate of f2 and wherein the total flow rate of the biological fluid through the laminar flow mixing device is f2×n which is about equal to the total flow rate of the biological fluid entering the laminar flow mixing device from a first tube;
    the first tube having a diameter A1 through which the biological fluid flows at a flow rate F1 and wherein F1>f2 and wherein n×$a_2$ is about equal to $A_1$;
    a second tube having an inner diameter A3 is in fluid communication with the plurality of tubes of the laminar flow mixing device via an outlet connecting the plurality of tubes with the second tube wherein the second tube is in fluid communication with a reverse-flow density gradient (RFDG) centrifuge having a rotor via the second tube wherein the flow rate in the second tube is F3 is about equal to F1; and
    the RFDG centrifuge rotor is capable of receiving the biological fluid mixed with the high density particles functionalized with the capture molecule from the mixing device via the second tube which is in fluid communication with the RFDG centrifuge and the mixing device.

2. The apparatus of claim 1 further comprising a pump for pumping the biological fluid through said laminar flow mixing device and a syringe pump located before said laminar flow mixing device for combining said high density particles with the biological fluid.

3. The apparatus of claim 1 wherein said centrifuge comprises a variable element, said element selected from the group consisting of spin rate, number of open outlet ports, and flow rate of liquid through each outlet port.

4. The apparatus of claim 1 wherein the plurality of straight tubes are positioned substantially in a horizontal position.

5. The apparatus of claim 1 wherein the plurality of straight tubes is between about 2-64 tubes.

6. The apparatus of claim 1 wherein the biological fluid is blood.

7. The apparatus of claim 1 wherein the apparatus accepts blood from a donor and returns the blood to the donor after aphaeresis treatment via aphaeresis tubing.

8. The apparatus of claim 1 wherein the apparatus has a total flow volume of the biological fluid of between 30-35 ml/min.

9. The apparatus of claim 1 wherein the first tube is in fluid communication with the plurality of straight tubes of the laminar flow mixing device via an inlet connecting the plurality of straight tubes with the first tube.

10. The apparatus of claim 9 wherein the inlet of the laminar flow mixing device is a funnel with a wider portion of the funnel adjacent the laminar flow mixing device.

11. The apparatus of claim 1 wherein the outlet of the laminar flow mixing device is a funnel with a wider portion of the funnel adjacent the laminar flow mixing device.

12. A device for transporting functionalized high density nanoparticles mixed with molecules of interest in a biological fluid during aphaeresis comprising:
   a plurality of straight tubes of "n" number arranged in parallel with each tube of the plurality of straight tubes being straight along their entire length and having an inner diameter of a2 and a length of l2;
   a mixing chamber having a circular cross section upstream of the plurality of straight tubes, the mixing chamber having a first inlet and a second inlet wherein i) the high density nanoparticles enter the mixing chamber at the first inlet and ii) the biological fluid containing molecules of interest enter the mixing chamber at the second inlet and i) and ii) are mixed in a laminar manner within the mixing chamber to produce a resulting mixture that enters the plurality of tubes at a volume flow rate of F1 wherein each tube of the plurality of straight tubes is configured to carry a flow of the resulting mixture at a volume flow rate of f2 and wherein a total flow rate of the fluid through the device is f2×n=F1 from which the resulting mixture in each of the plurality of tubes drains into a receiving area at volume flow rate of f2×n≈F1≈F3, the receiving area has a single exit through which the resulting mixture exits at a volume flow rate of F3 wherein a2 has an inner diameter of 1.5 to 3 mm and l2 has a length of 0.001 to 240 meters ("m").

13. The device of claim 12 wherein the plurality of straight tubes are between 2-64.

14. The device of claim 12 wherein the length of the plurality of straight tubes is between about 0.001-24 m.

15. The device of claim 12 wherein the plurality of straight tubes are in fluid communication with the spherical mixing chamber and an exit funnel.

16. The device of claim 12 wherein there are no spiral elements in the mixing device.

17. A method of mixing functionalized nanoparticles with a flowing biological fluid in the apparatus of claim 1 wherein the flowing biological fluid includes a target analyte, functionalized nanoparticles, and a biological fluid, the method comprises:
   introducing to the mixing chamber i) the biological fluid containing a target analyte and ii) a solution containing functionalized nanoparticles having a capture molecule that specifically binds the target analyte when i) and ii) are mixed;
   passing the fluid mixture to the plurality (n) of straight tubes arranged in parallel with each tube of the plurality of straight tubes having an inner diameter of a2 and a length of l2 through which each tube of the plurality of straight tubes permits stable laminar flow of the fluid mixture at a flow rate of f2 and wherein the total flow rate of the fluid mixture through the plurality of tubes is f2×n which is about equal to the total flow rate of the fluids entering the mixing chamber device;
   each tube having a diameter A1 through which fluid mixture flows at a volume flow rate F1 and wherein F1>f2 and wherein n×a2 is about equal to A1; and
   flowing within the plurality of straight tubes the fluid mixture for a predetermined time period to allow coupling of the functionalized nanoparticle with the target analyte to produce a reaction rate that is faster than can occur using only gentle end-to-end mixing for the same time and concentrations of functionalized nanoparticle and the target analyte in the fluid mixture.

* * * * *